(12) United States Patent
Phillips

(10) Patent No.: US 10,485,351 B2
(45) Date of Patent: Nov. 26, 2019

(54) HEADBOARD APPARATUS FOR HOLDING A DECORATIVE COVER

(71) Applicant: Roderick William Phillips, Vancouver (CA)

(72) Inventor: Roderick William Phillips, Vancouver (CA)

(*) Notice: Subject to any disclaimer, the term of this patent is extended or adjusted under 35 U.S.C. 154(b) by 316 days.

(21) Appl. No.: 15/276,638

(22) Filed: Sep. 26, 2016

(65) Prior Publication Data

US 2017/0007031 A1    Jan. 12, 2017

Related U.S. Application Data

(62) Division of application No. 14/114,900, filed as application No. PCT/CA2012/000389 on Apr. 26, 2012, now abandoned.

(Continued)

(51) Int. Cl.
*A47C 19/02* (2006.01)
*A47C 31/00* (2006.01)
(Continued)

(52) U.S. Cl.
CPC ......... *A47C 19/022* (2013.01); *A01M 1/2011* (2013.01); *A01N 25/00* (2013.01);
(Continued)

(58) Field of Classification Search
CPC ... A47C 19/022; A47C 31/023; A47C 31/007; F16B 12/54
See application file for complete search history.

(56) References Cited

U.S. PATENT DOCUMENTS 1,569,710 A    1/1926  Burt
2,095,459 A *  10/1937 Tottenham ........... A47C 19/022
                                                    128/893
(Continued)

FOREIGN PATENT DOCUMENTS

CA    1112158 A1    11/1981
CA    2149164 A1    11/1996
(Continued)

OTHER PUBLICATIONS

International Search Report dated Feb. 13, 2013, from PCT Application No. PCT/CA2012/001015 (4 pages).
(Continued)

*Primary Examiner* — Michael Safavi
(74) *Attorney, Agent, or Firm* — Kilpatrick Townsend & Stockton LLP

(57) ABSTRACT

An apparatus for holding a decorative cover. The apparatus includes a body having front and rear opposite sides, the front side of the body having a front surface having a perimeter, the rear side of the body having a rear surface, and the body having an outwardly facing lateral surface between the front and rear surfaces; and a first connector on the body, the first connector detachably connectable, continuously adjacent at least a portion of the perimeter of the front surface, to a second connector, complementary to the first connector, on the decorative cover. A furniture apparatus includes at least one substantially thermoplastic body and one or both of diatomaceous earth and a PA1b-related peptide incorporated in one or more of the at least one body.

21 Claims, 26 Drawing Sheets

Related U.S. Application Data

(60) Provisional application No. 61/482,067, filed on May 3, 2011, provisional application No. 61/563,220, filed on Nov. 23, 2011.

(51) Int. Cl.

| | | |
|---|---|---|
| *A01N 61/00* | (2006.01) | |
| *A01M 1/20* | (2006.01) | |
| *A47C 19/00* | (2006.01) | |
| *A01N 25/00* | (2006.01) | |
| *A47B 13/08* | (2006.01) | |
| *F16B 12/54* | (2006.01) | |
| *A01N 65/20* | (2009.01) | |

(52) U.S. Cl.
CPC .............. *A01N 61/00* (2013.01); *A47B 13/08* (2013.01); *A47C 19/005* (2013.01); *A47C 19/021* (2013.01); *A47C 31/007* (2013.01); *F16B 12/54* (2013.01); *A01N 65/20* (2013.01)

(56) References Cited

U.S. PATENT DOCUMENTS

| | | | |
|---|---|---|---|
| 2,508,506 A * | 5/1950 | Fridolph | A47C 19/022 160/135 |
| 2,579,157 A * | 12/1951 | Price, Sr. | E04C 2/292 29/453 |
| 2,671,910 A * | 3/1954 | Wallen | A47C 19/022 403/289 |
| 2,687,537 A | 8/1954 | Wallace et al. | |
| 3,000,779 A | 9/1961 | Goodhue et al. | |
| 3,010,615 A | 11/1961 | Smith et al. | |
| 3,062,709 A | 11/1962 | Ordas | |
| 3,082,147 A | 3/1963 | Newallis et al. | |
| 3,082,148 A | 3/1963 | Baker et al. | |
| 3,132,769 A | 5/1964 | Zehrbach | |
| 3,165,441 A | 1/1965 | Ludvik et al. | |
| 3,306,499 A | 2/1967 | Lykes | |
| 3,652,425 A | 3/1972 | Wilson | |
| 3,676,279 A * | 7/1972 | Beaver | A47B 13/08 108/161 |
| 3,736,603 A * | 6/1973 | Rothman | A47C 19/022 446/72 |
| 3,878,147 A | 4/1975 | Craven | |
| 3,992,839 A * | 11/1976 | La Borde | E04B 2/721 52/275 |
| 4,008,688 A | 2/1977 | Nicholas | |
| 4,083,977 A | 4/1978 | Miesel | |
| 4,098,435 A | 7/1978 | Weyn | |
| 4,279,895 A | 7/1981 | Carle | |
| 4,526,305 A | 7/1985 | Lykes | |
| D286,378 S | 10/1986 | Banfield | |
| 4,683,674 A * | 8/1987 | Faul | A01G 9/022 47/83 |
| 4,702,046 A * | 10/1987 | Haugen | E04B 1/10 181/286 |
| 4,706,422 A * | 11/1987 | Ashton | E04B 2/7411 181/284 |
| 4,810,590 A * | 3/1989 | Rich | C08K 3/36 264/272.11 |
| 4,821,349 A | 4/1989 | Cohen | |
| 4,871,218 A * | 10/1989 | Swinson | A47F 7/147 312/312 |
| 4,957,395 A * | 9/1990 | Nelson | E02D 29/0266 405/285 |
| 5,074,348 A | 12/1991 | Phillips | |
| 5,176,435 A | 1/1993 | Pipkens | |
| 5,186,935 A | 2/1993 | Tucker | |
| 5,195,195 A * | 3/1993 | Murray | A47C 19/022 5/406 |
| 5,269,032 A * | 12/1993 | Flocks | A47C 19/022 5/280 |
| 5,308,613 A | 5/1994 | Banfield | |
| 5,346,296 A | 9/1994 | Kelley | |
| 5,439,690 A | 8/1995 | Knight | |
| 5,529,380 A * | 6/1996 | Blansett | A47C 4/02 297/440.23 |
| 5,693,344 A | 12/1997 | Knight et al. | |
| 5,773,017 A | 6/1998 | Korunic et al. | |
| 5,809,708 A | 9/1998 | Greer et al. | |
| 5,881,508 A * | 3/1999 | Irvine | E01C 5/20 405/219 |
| 6,004,569 A | 12/1999 | Bessette et al. | |
| 6,114,384 A | 9/2000 | Bessette et al. | |
| 6,182,307 B1 | 2/2001 | Rutrick | |
| 6,183,767 B1 | 2/2001 | Bessette et al. | |
| 6,196,156 B1 | 3/2001 | Denesuk et al. | |
| 6,263,529 B1 * | 7/2001 | Chadwick | A47C 21/08 5/414 |
| 6,276,102 B1 | 8/2001 | Shipman et al. | |
| 6,329,433 B1 | 12/2001 | Bessette et al. | |
| 6,331,572 B1 | 12/2001 | Bessette et al. | |
| 6,333,360 B1 | 12/2001 | Bessette et al. | |
| 6,340,710 B1 | 1/2002 | Bessette et al. | |
| 6,342,535 B1 | 1/2002 | Bessette et al. | |
| 6,342,536 B1 | 1/2002 | Bessette et al. | |
| 6,371,190 B1 | 4/2002 | Owens | |
| 6,372,801 B1 | 4/2002 | Bessette et al. | |
| 6,372,803 B1 | 4/2002 | Bessette et al. | |
| 6,375,969 B1 | 4/2002 | Kostka et al. | |
| 6,376,556 B1 | 4/2002 | Bessette et al. | |
| 6,394,321 B1 | 5/2002 | Bayer | |
| 6,395,789 B1 | 5/2002 | Bessette et al. | |
| 6,405,491 B1 | 6/2002 | Gallant | |
| 6,416,775 B1 | 7/2002 | Kostka et al. | |
| 6,506,409 B1 | 1/2003 | Hoy et al. | |
| 6,530,181 B1 | 3/2003 | Seiber et al. | |
| 6,531,163 B1 | 3/2003 | Bessette et al. | |
| 6,534,099 B1 | 3/2003 | Bessette et al. | |
| 6,543,071 B1 | 4/2003 | Lenner | |
| 6,550,083 B1 * | 4/2003 | LaMantia | A47C 29/003 135/96 |
| 6,581,807 B1 | 6/2003 | Mekata | |
| 6,618,876 B2 | 9/2003 | Murphy et al. | |
| 6,658,677 B2 | 12/2003 | Paul | |
| 6,713,518 B1 | 3/2004 | Bessette et al. | |
| 6,799,337 B1 * | 10/2004 | Raphael-Davis | A47D 7/00 5/658 |
| 6,849,614 B1 | 2/2005 | Bessette et al. | |
| 6,986,898 B1 | 1/2006 | Bessette | |
| 7,118,179 B1 | 10/2006 | Wilson et al. | |
| 7,159,253 B2 | 1/2007 | Yang | |
| 7,252,041 B2 * | 8/2007 | Overholt | C08K 3/22 108/57.25 |
| 7,387,151 B1 | 6/2008 | Payne | |
| 7,434,365 B2 * | 10/2008 | Geller | A47B 88/0044 220/315 |
| 7,487,558 B2 * | 2/2009 | Risk, Jr. | A61G 7/0536 5/280 |
| 7,490,509 B2 | 2/2009 | Bohmer | |
| 7,614,298 B2 | 11/2009 | Bohmer | |
| 7,624,465 B2 | 12/2009 | Oh | |
| 7,744,298 B2 | 6/2010 | Haas et al. | |
| 8,101,408 B2 | 1/2012 | Taylor et al. | |
| 8,205,378 B2 | 6/2012 | Banfield | |
| 8,215,051 B2 | 7/2012 | Alexander et al. | |
| 8,215,065 B2 | 7/2012 | Gallant | |
| 8,440,009 B2 | 5/2013 | Mahan | |
| 8,501,247 B2 | 8/2013 | Enan et al. | |
| 8,522,488 B1 | 9/2013 | Newkirk et al. | |
| D692,089 S | 10/2013 | Rubel et al. | |
| 8,551,235 B2 | 10/2013 | Mahan et al. | |
| 8,707,615 B2 | 4/2014 | Cullen | |
| 8,852,501 B2 | 10/2014 | Hedman | |
| 8,959,684 B2 * | 2/2015 | Oyo-Hoffmann | A47C 19/022 5/183 |
| 2002/0170256 A1 * | 11/2002 | Annaka | A47C 19/022 52/415 |
| 2003/0036530 A1 | 2/2003 | Bessette | |
| 2003/0039674 A1 | 2/2003 | Bessette | |
| 2003/0056587 A1 | 3/2003 | Carpenter et al. | |

(56) References Cited

U.S. PATENT DOCUMENTS

| | | |
|---|---|---|
| 2003/0061758 A1 | 4/2003 | Wilson |
| 2003/0194454 A1 | 10/2003 | Bessette et al. |
| 2004/0175407 A1 | 9/2004 | McDaniel |
| 2005/0004233 A1 | 1/2005 | Bessette et al. |
| 2005/0102921 A1* | 5/2005 | Mischo ............... A01G 9/033 52/79.1 |
| 2005/0132500 A1 | 6/2005 | Karl et al. |
| 2005/0136089 A1 | 6/2005 | Bessette et al. |
| 2005/0143260 A1 | 6/2005 | Bessette et al. |
| 2005/0147636 A1 | 7/2005 | Bessette et al. |
| 2005/0163869 A1 | 7/2005 | Bessette et al. |
| 2005/0170024 A1 | 8/2005 | Bessette et al. |
| 2005/0170025 A1 | 8/2005 | Bessette et al. |
| 2005/0170026 A1 | 8/2005 | Bessette et al. |
| 2005/0220662 A1 | 10/2005 | Hedman |
| 2005/0255139 A1* | 11/2005 | Hurd ..................... A01N 59/00 424/405 |
| 2005/0260241 A1 | 11/2005 | Bessette et al. |
| 2005/0260242 A1 | 11/2005 | Bessette et al. |
| 2005/0279033 A1 | 12/2005 | Faber et al. |
| 2006/0088564 A1 | 4/2006 | Bessette |
| 2006/0115507 A1 | 6/2006 | Bessette |
| 2006/0115508 A1 | 6/2006 | Bessette |
| 2006/0115509 A1 | 6/2006 | Bessette |
| 2006/0115510 A1 | 6/2006 | Bessette |
| 2006/0121074 A1 | 6/2006 | Bessette |
| 2006/0216367 A1* | 9/2006 | Taylor .................. A01N 65/00 424/757 |
| 2006/0270561 A1 | 11/2006 | Keim et al. |
| 2007/0094794 A1* | 5/2007 | Ellis ..................... A47G 9/007 5/482 |
| 2007/0164059 A1 | 7/2007 | Rosiello et al. |
| 2007/0193171 A1* | 8/2007 | Finerman ............. B05D 3/108 52/459 |
| 2007/0193699 A1 | 8/2007 | Repp et al. |
| 2007/0196412 A1 | 8/2007 | Karl et al. |
| 2007/0207221 A1 | 9/2007 | Bessette et al. |
| 2007/0289225 A1 | 12/2007 | Kern et al. |
| 2007/0298131 A1 | 12/2007 | Bessette et al. |
| 2007/0299037 A1 | 12/2007 | Bessette et al. |
| 2007/0299038 A1 | 12/2007 | Bessette et al. |
| 2008/0003315 A1 | 1/2008 | Bessette et al. |
| 2008/0003316 A1 | 1/2008 | Bessette et al. |
| 2008/0003317 A1 | 1/2008 | Bessette et al. |
| 2008/0004240 A1 | 1/2008 | Bessette et al. |
| 2008/0015167 A1 | 1/2008 | Bessette et al. |
| 2008/0038383 A1 | 2/2008 | Bessette et al. |
| 2008/0044481 A1 | 2/2008 | Harel |
| 2008/0054020 A1 | 3/2008 | Pierson et al. |
| 2008/0143227 A1* | 6/2008 | Kim ....................... F25D 23/02 312/405 |
| 2008/0153904 A1 | 6/2008 | Bessette |
| 2008/0181969 A1* | 7/2008 | Blanton ................. C08K 3/005 424/618 |
| 2008/0190088 A1 | 8/2008 | Chou |
| 2008/0193387 A1 | 8/2008 | De Wolff |
| 2008/0305134 A1* | 12/2008 | Lucas ................... A01N 25/34 424/403 |
| 2009/0031499 A1* | 2/2009 | Mervar ................. A61G 7/075 5/647 |
| 2009/0126257 A1 | 5/2009 | Banfield |
| 2009/0222995 A1 | 9/2009 | Perry et al. |
| 2009/0233940 A1 | 9/2009 | Taylor |
| 2009/0269381 A1 | 10/2009 | Schilling et al. |
| 2010/0009912 A1 | 1/2010 | Taylor et al. |
| 2010/0056656 A1 | 3/2010 | Matsuoka et al. |
| 2010/0127224 A1 | 5/2010 | Neff |
| 2010/0239679 A1 | 9/2010 | Greene et al. |
| 2010/0260866 A1 | 10/2010 | Lu |
| 2010/0264165 A1 | 10/2010 | Hansen et al. |
| 2011/0070322 A1 | 3/2011 | Bessette et al. |
| 2011/0124502 A1 | 5/2011 | Enan |
| 2011/0135764 A1 | 6/2011 | Enan |
| 2011/0146133 A1 | 6/2011 | Bunker et al. |
| 2011/0226711 A1* | 9/2011 | Okanishi ........... H01L 21/67333 211/41.1 |
| 2011/0236589 A1 | 9/2011 | Streisfeld |
| 2011/0256198 A1 | 10/2011 | Sonneck et al. |
| 2011/0311603 A1 | 12/2011 | Lucas |
| 2012/0048145 A1 | 3/2012 | Wang et al. |
| 2012/0167309 A1 | 7/2012 | Heidorn |
| 2012/0227313 A1 | 9/2012 | Mozeika, III et al. |
| 2012/0258150 A1* | 10/2012 | Rauckhorst ............ C11D 3/505 424/401 |
| 2012/0285076 A1 | 11/2012 | Banfield |
| 2013/0025185 A1 | 1/2013 | O'Connor |
| 2013/0089578 A1 | 4/2013 | Sumulong et al. |
| 2013/0142893 A1 | 6/2013 | Bessette et al. |
| 2013/0161060 A1 | 6/2013 | Ponce Ibarra et al. |
| 2014/0020280 A1 | 1/2014 | Cullen |
| 2014/0041285 A1 | 2/2014 | Russell et al. |
| 2014/0084774 A1 | 3/2014 | Phillips |
| 2014/0221528 A1 | 8/2014 | Ribi |
| 2014/0259879 A1 | 9/2014 | Logsdon |
| 2014/0323539 A1 | 10/2014 | Dieleman et al. |
| 2014/0357489 A1 | 12/2014 | Dieleman et al. |
| 2015/0007486 A1 | 1/2015 | Backmark et al. |
| 2015/0132412 A1 | 5/2015 | Bessette et al. |
| 2015/0132413 A1 | 5/2015 | Bessette et al. |
| 2015/0140136 A1 | 5/2015 | Bessette et al. |
| 2015/0289495 A1 | 10/2015 | Olszak |
| 2015/0368866 A1* | 12/2015 | Hydock ................. E01C 13/02 165/45 |
| 2016/0029616 A1 | 2/2016 | Johnston |
| 2017/0118998 A1 | 5/2017 | Bessette et al. |

FOREIGN PATENT DOCUMENTS

| | | |
|---|---|---|
| CA | 2163246 C | 2/2000 |
| CA | 2264383 A1 | 9/2000 |
| CN | 1550177 A | 12/2004 |
| CN | 2750730 Y | 1/2006 |
| CN | 200983804 Y | 12/2007 |
| CN | 201012152 Y | 1/2008 |
| CN | 101147643 A | 3/2008 |
| CN | 101381473 A | 3/2009 |
| CN | 201375245 Y | 1/2010 |
| CN | 201641161 U | 11/2010 |
| EP | 0412832 A2 | 2/1991 |
| EP | 429849 A2 | 6/1991 |
| EP | 2096141 A1 | 9/2009 |
| GB | 658221 | 10/1951 |
| GB | 673877 | 6/1952 |
| GB | 803611 A | 10/1958 |
| GB | 989014 | 4/1965 |
| GB | 998604 | 7/1965 |
| GB | 1521714 | 8/1978 |
| GB | 2107978 A | 5/1983 |
| GB | 2180449 A | 4/1987 |
| GB | 2370224 A | 6/2002 |
| GB | 2398007 A | 8/2004 |
| JP | 60-241406 A | 11/1985 |
| JP | H01365713 A | 7/1991 |
| JP | 08173296 A | 7/1996 |
| JP | 1015038 A | 6/1998 |
| JP | 11-292704 A | 10/1999 |
| JP | 2000-176370 A | 6/2000 |
| JP | 2004049366 A | 2/2004 |
| JP | 2005053813 A | 3/2005 |
| JP | 2010-208994 A | 9/2010 |
| JP | 2011524874 A | 9/2011 |
| WO | 94/27434 A1 | 12/1994 |
| WO | 9636220 A2 | 11/1996 |
| WO | 98/54971 A1 | 12/1998 |
| WO | 00/05964 A1 | 2/2000 |
| WO | 00/15033 A1 | 3/2000 |
| WO | 00/51433 A1 | 9/2000 |
| WO | 01/00026 A1 | 1/2001 |
| WO | 01/00032 A1 | 1/2001 |
| WO | 01/00034 A1 | 1/2001 |
| WO | 01/60163 A2 | 8/2001 |
| WO | 01/91554 A1 | 12/2001 |
| WO | 01/91556 A2 | 12/2001 |

(56) References Cited

FOREIGN PATENT DOCUMENTS

| WO | 2009017938 A1 | 2/2009 |
|---|---|---|
| WO | 2009045941 A1 | 4/2009 |
| WO | 2009058707 A1 | 5/2009 |
| WO | 2009117623 A2 | 9/2009 |
| WO | 2009153231 A2 | 12/2009 |
| WO | 2011146663 A2 | 11/2011 |
| WO | 2012149636 A1 | 11/2012 |
| WO | 2013/055773 A1 | 4/2013 |
| WO | 2013050967 A1 | 4/2013 |
| WO | 2013075212 A1 | 5/2013 |
| WO | 2013/083372 A1 | 6/2013 |
| WO | 2013101298 A1 | 7/2013 |
| WO | 2013160898 A1 | 10/2013 |

OTHER PUBLICATIONS

International Preliminary Report on Patentability dated Nov. 14, 2013, from PCT Application No. PCT/CA2012/000389 (6 pages).

International Search Report dated Aug. 8, 2012, from PCT Application No. PCT/CA2012/000389 (4 pages).

"The Benefits of Diatomaceaous Earth" accessed at http://www.offthegridnews.com on Jun. 30, 2014, 2 pages.

Aerosol tops 6, downloaded from http://en.wikipedia.org/wiki/File:Aerosol_tops_6.svg, Mar. 6, 2007.

Agrium Advanced Technologies, Material Data Safety Sheet, PRO® Green Earth S. D. Insect Dust, Nov. 2010.

Akhtar et al., Horizontal Transfer of Diatomaceous Earth and Botanical Insecticides in the Common Bed Bug, Cimex lectularius L.; Hemiptera: Cimicidae, Sep. 25, 2013, PLoS ONE 8(9): e75626. doi:10.1371/journal.pone.0075626.

Akhtar, Toxicity data for De 51 and DE 53 against bed bugs, Jun. 23, 2011.

American Diatomite Inc., downloaded from http://www.americandiatomite.com/ on Apr. 12, 2014, NV, USA.

Available Products, Diatomaceous Earth Hawaii, downloaded from http://www.diatomaceousearthhawaii.com/avaiable-products.html on Jun. 26, 2012.

Bacillariophyceae Algae, downloaded from http://web.biosci.utexas.edu/utex/algaeDetail.aspx?algaeID=6184, Apr. 5, 2006, University of Texas at Austin, Austin, TX, USA.

BadBedBugs.com, Bed Bug Dust: Diatomaceous Earth (DE) is a Natural Solution You Can Buy Anywhere, 2008-2014, downloaded from http://www.badbedbugs.com/bed-bug-dust/ on Jan. 4, 2014.

Barrentine, NEW-OA2ki (DE) in a can!!, from http://www.barrettine.co.uk/Environmental-Health/index.php?option=com_content&view=article&id=92:oa2ki-aerosol&catid=1:latest-news&Itemid=18 and dated Oct. 24, 2011 on http://web.archive.org/, Barrentine, United Kingdom.

BASF, The Chemical Company, Better Products for Pest Control Product List, BASF The Chemical Company, USA, downloaded from http://pestcontrol.basf.us/products/product-index.html on Mar. 19, 2012.

Berg, Bed bugs: The pesticide dilemma, Journal of Environmental Health, Jun. 1, 2010, pp. 32-35, vol. 72, National Environmental Health Association, Denver, CO, USA.

Canada, MotherEarth D Pest Control Dust, Nov. 22, 2012, Pest Management Regulatory Agency, Canada.

Canadian Center for the Culture of Microorganisms, downloaded from http://www3.botany.ubc.ca/cccm/, May 28, 2001, University of British Columbia, Vancouver, BC, Canada.

Chen, Jiannen, "Introduction of a Introduction of a Novel Physical Insecticide (PG)," pp. 21 and 38, Jan. 1995. Foreign Article. Retrieved from the Internet in Oct. 2015 at http://www.cnki.net.

Diafil 610, EPA Reg. No. 73729-1, Feb. 13, 2003.

DiaSource Diatomaceous Earth, EPA Reg. No. 69261-5, Dec. 16, 2010.

Diatomaceous Earth General Fact Sheet, National Pesticide Information Center, retrieved from http://npic.orst.edu/factsheets/degen.html on Jan. 27, 2015, 4 pages.

Diatomaceous Earth Hawaii, downloaded from http://www.diatomaceousearthhawaii.com/ on Jun. 26, 2012.

Doggett, Stephen L. et al., "The efficacy of diatomeous earth against the common Bed Bug, Cimex lectularlus: A report for Mount Sylvia Diatomite," May 1, 2008, pp. 1-50, XP055205184, Retrieved from the Internet on Jul. 29, 2015 at http://mtsylviadiatomite.com.au/mod/files/documents/Final_bedbug_trial.pdf.

Domingue et al., Sexual dimorphism of arrestment and gregariousness in the bed bug (Cimex lectularius) in response to cuticular extracts from nymphal exuviae, Physiological Entomology, Sep. 2010, pp. 203-213, vol. 35, Issue No. 3, Wiley, Hoboken, NJ, USA.

Eagle-Picher Minerals, Inc., Crop Guard™, EPA Reg. No. 007655-1, Jan. 11, 1995, Reno, NV, USA.

Ecosmart, Bed Bugs, downloaded from http://ecosmart.com/bedbugs/ on Mar. 6, 2014, EcoSmart Technologies, Roswell, GA, USA.

EP Minerals, Celatom® FN & MN Grades, Material Safety Data Sheet, Jun. 10, 2010, EP Minerals, Reno, NV, USA.

EP Minerals, Celatom® MN-51, Technical Data Sheet, Oct. 2010, EP Minerals, Reno, NV, USA.

EP Minerals, Celatom® MN-53, Technical Data Sheet, Oct. 2010, EP Minerals, Reno, NV, USA.

Extended European Search Report dated Aug. 11, 2015, from European Application No. 12850927.0 (9 pages).

Extended European Search Report dated Sep. 2, 2014, from European Application No. 12779394.1 (5 pages).

Gagne et al., Questions on Registration Requirements for an End-use Diatomaceous Earth Product, 2013.

Harlan, Bed Bugs 101: the Basics of Cimex lectularius., American Entomologist, 2006, pp. 99-101, vol. 52, No. 2, Entomological Society of America, Annapolis, MD, USA.

Haynes et al., Bed bug deterrence, BMC Biology, Sep. 9, 2010, pp. 117-119, vol. 8, BioMed Central, Lexington, KY, USA.

Health Canada, Diatomaceous Earth in Aerosol, Pesticide Label Search, Feb. 15, 2012, Government of Canada, Canada.

Hopkins et al., Fresh Water, Food-Grade Diatomaceous Earth, 2004-2011, Best Prices Storable Foods, Quinlan, TX, USA, cited in International Search Report dated Feb. 13, 2013 in PCT/CA2012/001015 as being dated Oct. 25, 2011 at http://web.archive.org/web/20111025621O2/http://www.internet-grocer.net/diatome.htm.

Hopkins et al., Fresh Water, Food-Grade Diatomaceous Earth, 2004-2011, Best Prices Storable Foods, Quinlan, TX, USA, downloaded from http://www.internet-grocer.net/diatome.htm on Oct. 31, 2011.

Isman et al., Quantitative Phase Analysis of Diatomaceous Earth Using The Rietveld Method and X-Ray Powder Diffraction Data. Scanning Electron Microscope Images of Diatomaceous Earth, May 2, 2012, University of British Columbia, Vancouver, BC, Canada.

Isman et al., Quantitative Phase Analysis of Diatomaceous Earth Using the Rietveld Method and X-Ray Powder Diffraction Data. Scanning Electron Microscope Images of Diatomaceous Earth, May 22, 2012, University of British Columbia, Vancouver, BC, Canada.

Isman et al., Scanning Electron Microscope Images of Diatomaceous Earth, Jul. 16, 2012, University of British Columbia, Vancouver, BC, Canada.

Isman et al., Toxicity of different types of diatomaceous earth against the common bed bug, Cimex lectularius in the laboratory, Apr. 30, 2012, University of British Columbia, Vancouver, BC, Canada.

Isman, Residual toxcity of aerosol (51) against bed bugs, Feb. 1, 2012, University of British Columbia, Vancouver, BC, Canada.

Isman, Toxicity data for dust samples, Jul. 17, 2012, University of British Columbia, Vancouver, BC, Canada.

Isman, Toxicity data of different dusts, Feb. 18, 2012, University of British Columbia, Vancouver, BC, Canada.

JP Textiles, Headboards—Upholstered, Pricelist, 2008, JP Textiles, Vancouver, BC, Canada.

K-G Spray-Pak Inc, Gravimetric Determination of Solids Concentration (percent active) in JP Bed Bug Killer, Jun. 20, 2012.

Kobylnyk, Similar Registered Product, Nov. 21, 2011.

Korunic, Diatomaceous Earths, a Group of Natural Insecticides, Journal of Stored Products Research, 1998, pp. 87-97, vol. 34, Issue No. 2-3, Elsevier Science, United Kingdom.

(56) References Cited

OTHER PUBLICATIONS

Korunic, Rapid Assessment of the Insecticidal Value of Diatomaceous Earths Without Conducting Bioassays, Journal of Stored Products Research, 1997, pp. 219-229, vol. 33, No. 3, Elsevier Science, United Kingdom.
Lebeau, T. et al., "Diatom cultivation and biotechnolgically relevant products. Part II: Current and Putative Products," Applied Microbiology and Biotechnology, 2003, vol. 60, issue 6, pp. 624-632.
Malvern Instruments, EP51 Result Analysis Report, Oct. 30, 2012, Malvern Instruments Ltd., Malvern, UK.
Malvern Instruments, Mother Earth Result Analysis Report, Oct. 30, 2012, Malvern Instruments Ltd., Malvern, UK.
Mann, David G., "Raphid diatoms", Tree of Life Web Project, Feb. 7, 2010, pp. 1-4, XP055205449, Retrieved from the Internet Jul. 30, 2015 at http://tolweb.org/raphid_diatoms/125307.
McGrath, Is Diatomaceous Earth Harmful?, Demand Media, USA, 1999-2013, downloaded from http://www.ehow.com/about_6571034_diatomaceous-earth-harmful_.html on Nov. 7, 2013.
Moore et al., Laboratory Evaluations of Insecticide Product Efficacy for Control of Cimex lectularius, Journal of Economic Entomology, Dec. 2006, pp. 2080-2086, vol. 99, No. 6, Entomological Society of America, Annapolis, MD, USA.
One Stop Grow Shop, Crop Guard—DustOff PM 250MIs, downloaded from http://www.onestopgrowshop.co.uk/pest-and-disease-control/leaf-and-flower-mould-rot-control-en/crop-guard-dustoff-pm-250mls.html on Apr. 18, 2014, Stoke-on-Trent, Staffordshire, UK.
Pereira, Lethal effects of heat and use of localized heat treatment for control of bed bug infestations, Journal of Economic Entomology, Jun. 2009, pp. 1182-1188, vol. 102, No. 3, Entomological Society of America, Annapolis, MD, USA.
Pest Control Direct, Oa2ki Aerosol Pesticide Free Ant Killer Powder, United Kingdom, downloaded from http://www.pestcontroldirect.co.uk/acatalog/Oa2ki_Aerosol_500gm_Powder_in_a_Can_.html on Oct. 31, 2011.
Pest Control Direct, Pest Control Direct Reviews, United Kingdom, downloaded from http://www.feefo.com/GB/en/reviews/Pest-Control-Direct/?id=103607 on Oct. 31, 2011.
Pesticide Action Network, Crop guard, downloaded from http://www.pesticideinfo.org/Detail_Product.jsp?REG_NR=00765500001&DIST_NR=007655 on Apr. 8, 2014.
Power, Examination of sample EP51 by scanning electron microscopy, Aug. 9, 2012, University of British Columbia, Vancouver, BC, Canada.
Power, Review of Diatomaceous Earths in Table 3 of Korunic, a Group of Natural Insecticides, 1998, University of British Columbia, Vancouver, BC, Canada (2 pages).
ProGreen S.D. Insect Dust Label Notification Change, 2007-2008.
Reinhardt et al., Biology of the Bed Bugs (Cimicidae), Annual Review of Entomology, Sep. 1, 2006, pp. 351-374, vol. 52, Annual Reviews, Palo Alto, CA, USA.
Restriction Requirement dated Oct. 5, 2015, from U.S. Appl. No. 14/114,900 (5 pages).
Romero et al., Insecticide Resistance in the Bed Bug: A Factor in the Pest's Sudden Resurgence?, Journal of Medical Entomology, Mar. 2007, pp. 175-178, vol. 44, Entomological Society of America, Annapolis, MD, USA.
Sacred Mountain, Diatomaceous Earth, Sacred Mountain, Visalia, CA, USA, downloaded from http://sacredmountainjourney.com/id21.html on Nov. 7, 2013.
Synedra delicatissima sensu PR, downloaded from http://craticula.ncftac.uk/Eddi/jsp/showimage.jsp?TaxonId=XXG987 on Mar. 5, 2014, Newcastle University, United Kingdom.
The Company's Beginnings, Diatomaceous Earth Hawaii, downloaded from http://www.diatomaceousearthhawaii.com/the-companys-beginnings.html on Jun. 26, 2012 (2 pages).
Todd, Repellents for Protection from Bed Bugs: The Need, the Candidates, Safety Challenges, Test Methods and the Chance of Success, Recent Developments in Invertebrate Repellents, 2011, pp. 137-150, Chapter 9, ACS Publications, Washington, DC, USA.
Tui Rose, Going Green Using Diatomaceous Earth How-to-Tips, 2012, downloaded from http://www.tuirose.com/diatomaceous-earth-book-introduction.php on Nov. 7, 2013.
UTEX The Culture Collection of Algae, downloaded from http://web.biosci.utexas.edu/utex/ on Mar. 5, 2014, University of Texas at Austin, Austin, TX, USA.
Vayias et al., Evaluation of natural diatomaceous earth deposits from south-eastern Europe for stored-grain protection: the effect of particle size, published online Jun. 18, 2009, Pest Management Science, pp. 1118-1123, vol. 65, Society of Chemical Industry.
Wang et al., Case Study: Controlling Bed Bugs in Apartments, Pest Control Technology, Nov. 2007, pp. 64-70, vol. 35, GIE Media, Richfield, OH, USA.
Wang, Jingshing, "Diatomite Using Insecticide," p. 22, Jul. 1999. Foreign Article. Retrieved from the Internet in Oct. 2015 at http://www.cnki.net. Wang, Jingshing, "Diatomite Using Insecticide," p. 22, Jul. 1999. Foreign Article. Retrieved from the Internet in Oct. 2015 at http://www.cnki.net.
Watson, The Brutal Business of Battling Bedbugs, Sep. 12, 2010, Daily Finance, USA, downloaded from http://www.dailyfinance.com/2010/09/12/the-business-of-bedbugs/ on Apr. 19, 2011.
Weeks et al., A bioassay for studying behavioural responses of the common bed bug, *Cimex lectularius* (Hemiptera: Cimicidae) to bed bug-derived volatiles, Bulletin of Entomological Research, Jan. 27, 2010, pp. 1-8, vol. 101, Cambridge University, Cambridge, UK.
What is Diatomaceous Earth ( DE )?, Diatomaceous Earth Hawaii, downloaded from http://www.diatomaceousearthhawaii.com/what-is-diatomaceous-earth--de.html on Jun. 26, 2012.
Whitmire Micro-Gen Research Laboratories, Inc., Prescription Treatment® brand TRI-DIE®, 2005, St. Louis MO, USA.
Whitmire PT® 239 Tri Die Insecticide, EPA Registration No. 499-385, Aug. 29, 2013.
Search Opinion, dated Dec. 12, 2016, for corresponding European Patent Application No. EP12779394.1, 4 pages.

* cited by examiner

HEADBOARD APPARATUS FOR HOLDING A DECORATIVE COVER

CROSS-REFERENCES TO RELATED APPLICATIONS

This application is a divisional of U.S. application Ser. No. 14/114,900, filed Oct. 30, 2013, which is a National Stage of International Application No. PCT/CA2012/000389, filed Apr. 26, 2012, which claims the benefit of U.S. Provisional Application No. 61/482,067, filed May 3, 2011, and U.S. Provisional Application No. 61/563,220, filed Nov. 23, 2011, the entireties of which are incorporated by reference herein.

BACKGROUND

1. Field

The invention relates generally to an apparatus for holding a decorative cover, a kit and a system including the same, a headboard apparatus comprising a substantially thermoplastic body, a furniture apparatus comprising diatomaceous earth, legume extracts, or both, and use of one of the apparatuses, kits, or systems to control a population of animals.

2. Related Art

Many bedrooms in homes and hotels, for example, include headboards, which may be attached to a head of a bed, or which may be attached to a wall proximate the head of the bed. Many conventional headboards include a decorative cover upholstered to a wooden frame. However, wood is disadvantageously difficult to clean, and upholstered decorative covers may be difficult or impossible to replace. Generally, once an upholstered cover is removed from a frame, the cover will be significantly damaged where it was attached, and either not reusable or reusable only on a smaller frame. Therefore, if such a headboard becomes infested with *Cimex lectularius* (also known as "bedbugs") or if there is a desire to change the decorative cover for a new colour scheme, for example, then generally such conventional headboards must be discarded and replaced. Discarding and replacing headboards is wasteful and environmentally damaging, and may be very expensive or cost-prohibitive for large institutions such as hotels, for example. Further, in some institutions such as hotels for example, closing large parts or all of the hotel for bedbug or other pest removal can result in significant loss of revenue.

There have been attempts to attach decorative covers by techniques other than conventional upholstery. For example, U.S. Pat. No. 2,508,506 to Fridolph ("Fridolph") discloses receiving fastener heads, which are around a perimeter of a decorative panel, in respective recesses on a frame, and then in respective slots adjacent the recesses. The slots hold the fastener heads, and thus the decorative panel, to the frame. However, such a technique attaches the decorative panel only at discrete locations of the fastener heads, thereby leaving unsightly gaps along the perimeter of the decorative panel between the discrete locations where the decorative panel is attached. Further, to position the fastener heads in the slots, the fastener heads must be received in the respective recesses and then slid from the respective recesses into the adjacent slots. Disadvantageously, sliding the fastener heads from respective recesses into respective slots may require stretching or deforming the decorative panel. Further, the fastener heads may have to be spaced a minimum distance from the decorative panel to permit such sliding, and because of such spacing the fastener heads may not hold the decorative panel close to the frame. The decorative panel may therefore not be tightly held against the frame, disadvantageously giving the decorative panel a loose or saggy appearance. It is believed that at least because of such disadvantages, a headboard as disclosed by Fridolph would not be commercially viable and is unlikely to have been produced commercially.

Also, U.S. Pat. No. 5,195,195 to Murray ("Murray") discloses covering a front side of a headboard with fabric, and positioning tubing in a groove in a back side of the headboard to hold the fabric in the groove under the tubing. However, such a technique requires carefully positioning the fabric on the headboard, and maintaining the fabric in position while the tubing is positioned in the groove. Simultaneously holding the fabric and positioning the tubing is disadvantageously cumbersome and time-consuming. Again, it is believed that at least because of such disadvantages, a headboard as disclosed by Murray would not be commercially viable and is unlikely to have been produced commercially.

Some known methods of controlling bedbug and other pest populations involve using certain pesticides, but some pesticides may be harmful to humans and to other life. Other known methods of controlling bedbug populations include applying diatomaceous earth, but known methods of applying diatomaceous earth can be cumbersome. For example, known methods of applying diatomaceous earth may undesirably require handling the diatomaceous earth. Further, known methods may be sufficiently complex so as to require professional involvement, which may undesirably add to cost and delay of bedbug treatment.

SUMMARY

According to one illustrative embodiment, there is provided an apparatus for holding a decorative cover. The apparatus comprises: a body having front and rear opposite sides, the front side of the body having a front surface having a perimeter, the rear side of the body having a rear surface, and the body having an outwardly facing lateral surface between the front and rear surfaces; and a first connector on the body, the first connector detachably connectable, continuously adjacent at least a portion of the perimeter of the front surface, to a second connector, complementary to the first connector, on the decorative cover.

The first connector may be on the lateral surface. The first connector may comprise a hook side of a hook-and-loop connector. The first connector may comprise a loop side of a hook-and-loop connector.

The first connector may extend adjacent at least a majority of the perimeter of the front surface. The first connector may extend adjacent substantially the entire perimeter of the front surface.

The apparatus may further comprise a third connector for mounting the apparatus on a wall. The third connector may comprise a first edge on the rear side of the body for coupling with a complementary edge on a fourth connector mounted to the wall. The third connector may comprise a first plurality of spaced apart edges on the rear side of the body for coupling with respective complementary edges on the fourth connector.

The apparatus may further comprise a fifth connector for mounting the apparatus on a wall. The fifth connector may comprise a second edge on the rear side of the body for coupling with the complementary edge on the fourth connector. The second edge may extend non-parallel to the first edge. The second edge may extend perpendicular to the first edge. The fifth connector may comprise a second plurality of spaced apart edges on the rear side of the body for coupling with the respective complementary edges on the fourth connector.

The apparatus may further comprise a bed frame connector for connecting the body to a bed frame. The bed frame connector may comprise at least one receptacle defined by the body for receiving at least one respective support attachable to the bed frame.

The apparatus may further comprise a light source connector for connecting a light source proximate the lateral surface. The light source may comprise a plurality of lights in a light string, and the light source connector may comprise a plurality of clips for holding the light string proximate the lateral surface. The lateral surface of the body may comprise a translucent portion for transmitting light from the light source. The apparatus may further comprise a translucent cover connectable to the lateral surface of the body for covering the light source.

The body may define a storage compartment on the rear side of the body for storing objects.

The apparatus may further comprise an inclination measuring device for measuring inclination of the body. The inclination measuring device may comprise a bubble level.

The front surface may define a recess for receiving padding between the body and the decorative cover. The body may define a plurality of through-openings extending between the front and rear surfaces, the through-openings for receiving respective fasteners receivable through the padding and through the decorative cover to compress the padding in respective regions surrounding the respective fasteners. The front surface may comprise a generally flat planar portion and an inward-facing portion between the generally flat planar portion and the lateral surface of the body. The generally flat planar portion of the front surface and the inward-facing portion of the front surface may define the recess. An adjacent similar apparatus may be stackable against the rear side of the body. The body may define a first projection having the lateral surface and the inward-facing portion of the front surface, and at least a portion of the lateral surface may be positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus.

The body may define, on the rear surface, at least one additional projection configured to contact the adjacent similar apparatus when the adjacent similar apparatus is stacked against the rear side of the body.

The body may be substantially thermoplastic. The body may comprise carbon plastic. The body may comprise a PA1b-related peptide incorporated in the body. The body may further comprise saponin incorporated in the body. The body may comprise diatomaceous earth incorporated in the body. The diatomaceous earth may be about 30% by weight of the body.

According to another illustrative embodiment, there is provided a kit comprising the apparatus and the decorative cover.

According to another illustrative embodiment, there is provided a kit comprising the apparatus, the padding, and the decorative cover.

According to another illustrative embodiment, there is provided a system comprising the apparatus and the decorative cover, wherein the first connector is connected to the second connector such that the decorative cover covers at least a portion of the front surface of the body surrounded by the perimeter of the front surface of the body.

According to another illustrative embodiment, there is provided a system comprising the apparatus, the padding, and the decorative cover, wherein the first connector is connected to the second connector such that the decorative cover covers at least a portion of the front surface of the body surrounded by the perimeter of the front surface of the body, and such that the decorative cover holds the padding between the body and the decorative cover and in the recess for receiving padding.

According to another illustrative embodiment, there is provided a headboard apparatus comprising a substantially thermoplastic body having a holder for holding a decorative cover. The body may comprise carbon plastic.

According to another illustrative embodiment, there is provided a furniture apparatus comprising at least one substantially thermoplastic body and a PA1b-related peptide incorporated in one or more of the at least one body. The body may further comprise saponin incorporated in the body. The body may further comprise diatomaceous earth incorporated in the body. The diatomaceous earth may be about 30% by weight of the one or more of the at least one body. The at least one body may comprise carbon plastic.

According to another illustrative embodiment, there is provided a furniture apparatus comprising at least one substantially thermoplastic body and diatomaceous earth incorporated in one or more of the at least one body. The diatomaceous earth may be about 30% by weight of the one or more of the at least one body. The at least one body may comprise carbon plastic.

The furniture apparatus may comprise an apparatus for holding a decorative cover.

The furniture apparatus may comprise a bed. The at least one substantially thermoplastic body may comprise at least one support for contacting a floor of a room, and the bed may comprise a platform supportable by the at least one support and configured to support a mattress on the platform.

The furniture apparatus may comprise a table. The at least one substantially thermoplastic body may comprise at least one support for contacting a floor of a room, and the table may comprise a platform supportable by the at least one support.

The furniture apparatus may comprise a dresser or a nightstand.

The diatomaceous earth may comprise CELATOM™ MN-51. The diatomaceous earth may have a median particle diameter of about 15 microns. The diatomaceous earth may have a median particle diameter of more than about 14 microns. The diatomaceous earth may be about 5.6% CaO. The diatomaceous earth may comprise more than about 0.9% CaO. The diatomaceous earth may be about 7.8% $Al_2O_3$. The diatomaceous earth may comprise more than about 5.6% $Al_2O_3$. The diatomaceous earth may have a pH of about 7.5 in a 10% slurry. The diatomaceous earth may have a pH of more than about 7.0 in a 10% slurry. The diatomaceous earth may be about 73.6% $SiO_2$. The diatomaceous earth may be less than about 83.7% $SiO_2$. The diatomaceous earth may be about 1.8% $Fe_2O_3$. The diatomaceous earth may be less than about 2.3% $Fe_2O_3$. The diatomaceous earth may comprise less than about 5.0% $H_2O$ by weight. The diatomaceous earth may be about 3.0% $H_2O$ by weight. The diatomaceous earth may absorb water in an amount of about 165% by weight. The diatomaceous earth may be about 0.3% MgO. The diatomaceous earth may be heat-treated. The diatomaceous earth may be flash dried. The diatomaceous earth may be flash dried at about 480° C.

According to another illustrative embodiment, there is provided use of the apparatus, the kit, or the system to control one or more of a population of animals having exoskeletons, a population of arthropods, a population of arachnids, a population of insects, and a population of *Cimex lectularius*.

Other aspects and features will become apparent to those ordinarily skilled in the art upon review of the following description of specific embodiments in conjunction with the accompanying figures.

DETAILED DESCRIPTION

Figure 1:
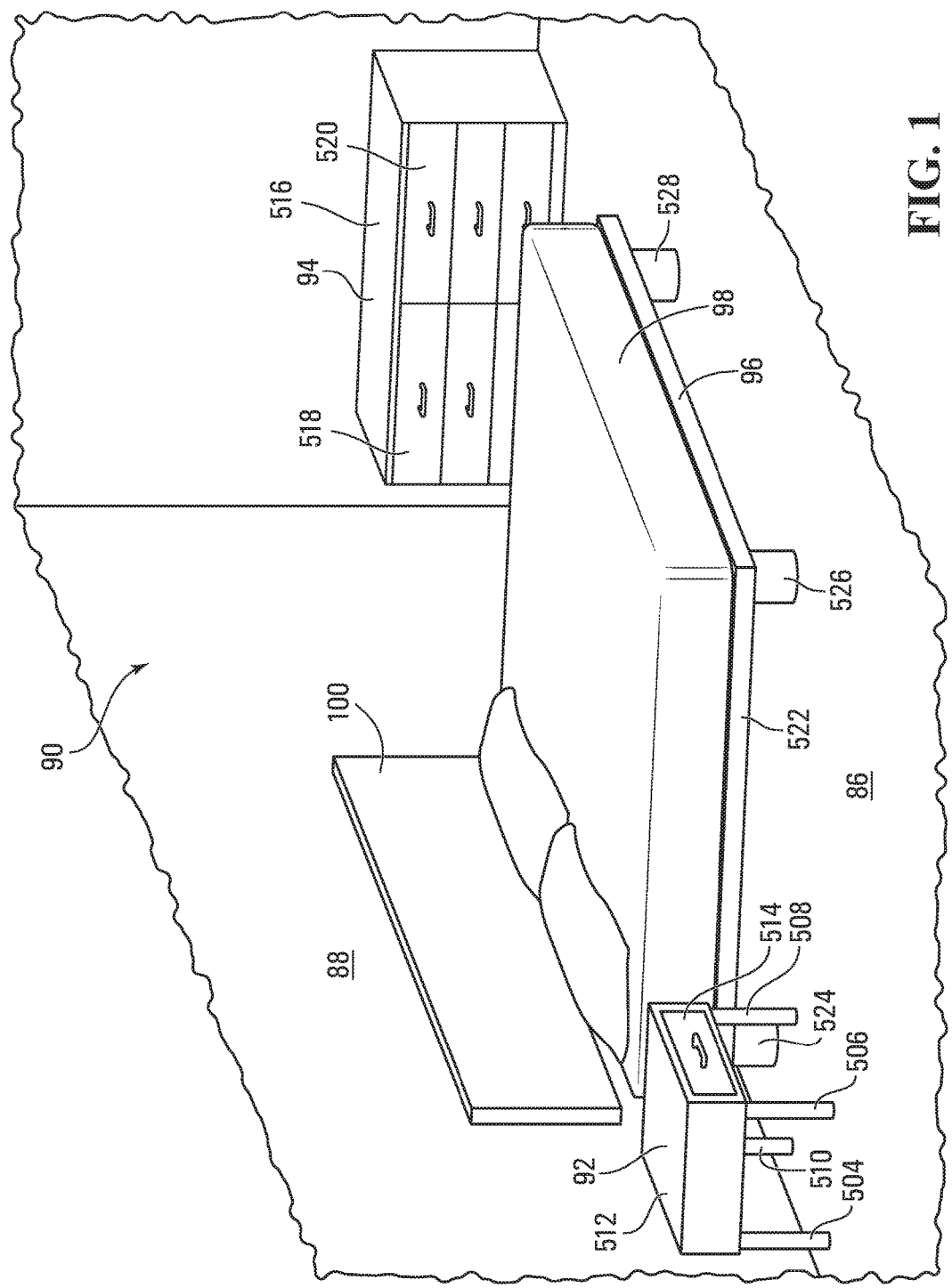
FIG. 1 is an oblique view of an illustrative room.

Referring to FIG. 1, an illustrative room includes a floor 86, a wall 88, and an illustrative furniture system shown generally at 90 and including a nightstand 92, a dresser 94, a bed 96, a mattress 98, and a headboard system 100.

Figure 2:
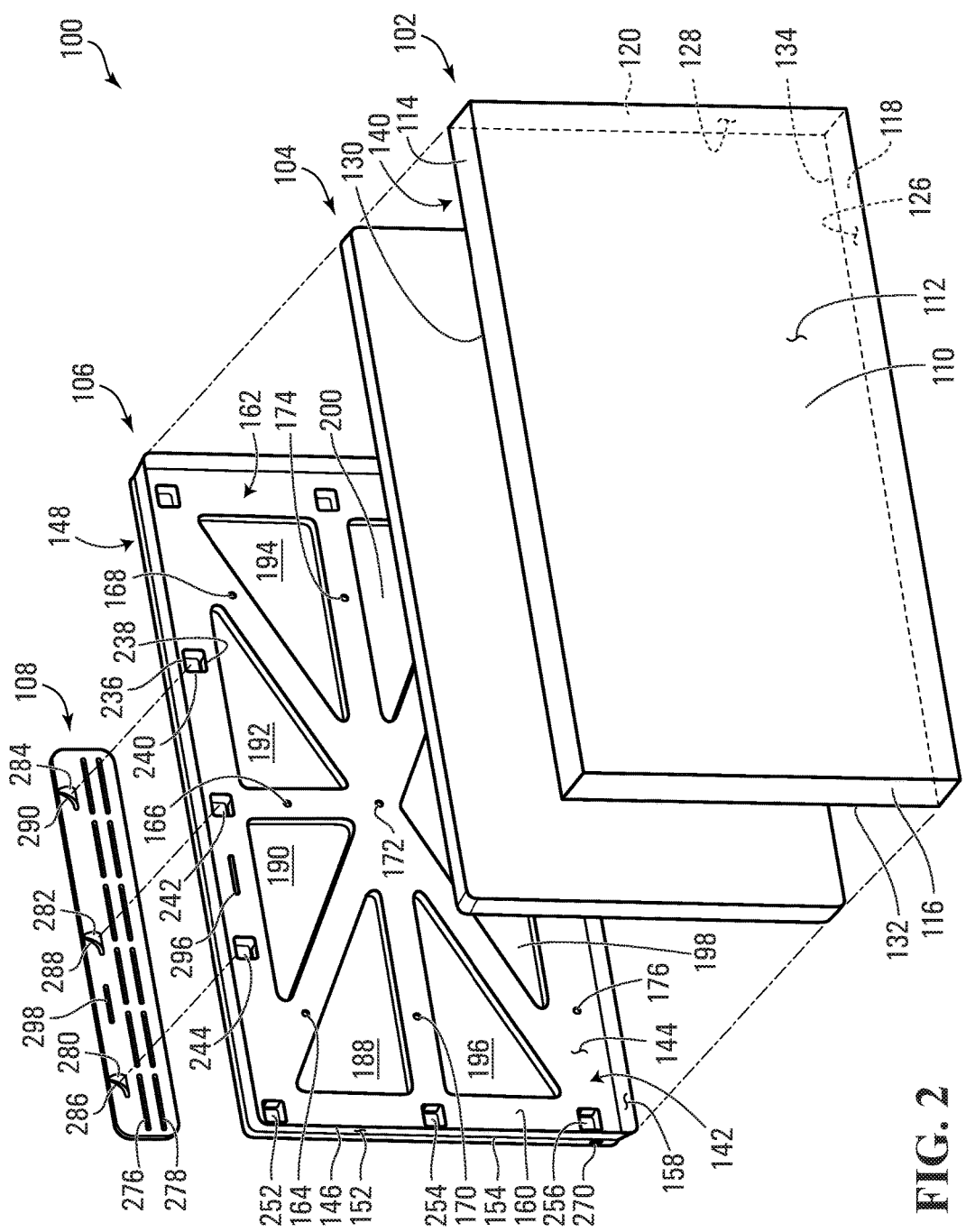
FIG. 2 is an exploded oblique view of a headboard system of the room of FIG. 1.

Referring to FIG. 2, the headboard system 100 includes a decorative cover 102, padding 104, a body 106, and a wall-mountable cleat 108. The decorative cover 102 in the embodiment shown includes a generally rectangular portion 110 having an outer surface 112. The outer surface 112 may include any decorative colours, ornamentation, or pattern, for example. The decorative cover 102 also includes lateral portions 114, 116, 118, and 120 extending generally from a perimeter of the generally rectangular portion 110 and generally perpendicular to the generally rectangular portion 110. The generally rectangular portion 110 and the lateral portions 114, 116, 118, and 120 may be made from any commonly available fabric and may be stitched together, for example.

Figure 3:
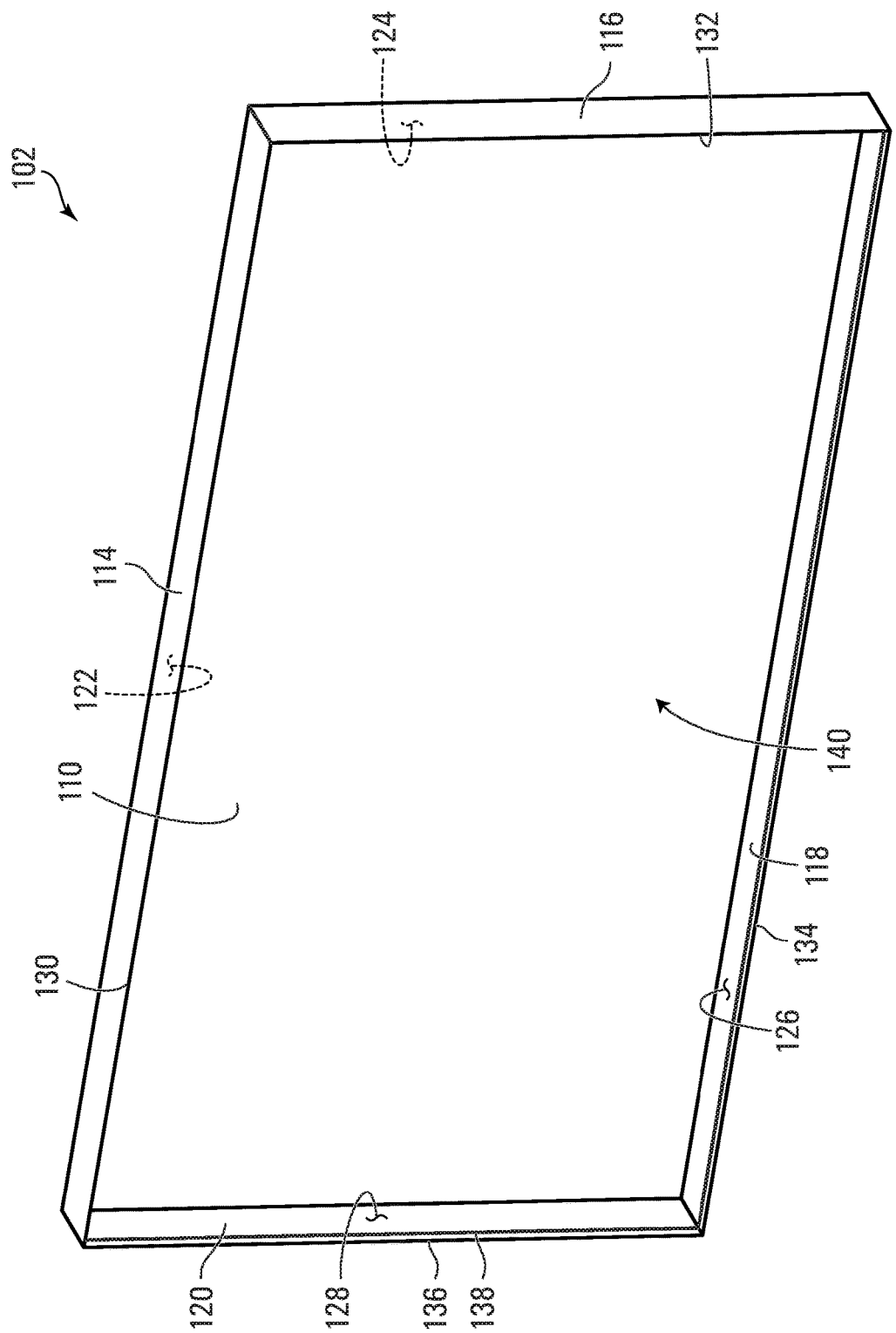
FIG. 3 is an oblique view of a decorative cover of the headboard system of FIG. 2.

Referring to FIG. 3, the lateral portions 114, 116, 118, and 120 have respective inner surfaces 122, 124, 126 and 128 facing the generally rectangular portion 110.

The lateral portions 114, 116, 118, and 120 also have respective outer edges 130, 132, 134, and 136. The decorative cover 102 also has a connector 138 on the inner surfaces 122, 124, 126, and 128 proximate the outer edges 130, 132, 134, and 136. In the embodiment shown, the connector 138 is a so-called "loop side" of a hook-and-loop connector, such as the hook-and-loop connector commonly known as VELCRO™ for example.

Referring back to FIG. 2, the padding 104 in the embodiment shown includes a generally rectangular body made from one or more of many commonly available foam materials. In alternative embodiments, the padding 104 may include an air bladder or feather padding, for example. Therefore the padding 104 in some embodiments may be selected to avoid undesired allergens, for example. The padding 104 may include a fire-retardant substance as may be required by law. Further, the padding 104 is sized to be received in a recess shown generally at 140 in FIG. 3 and defined by the generally rectangular portion 110 and the lateral portions 114, 116, 118, and 120 of the decorative cover 102.

Figure 4:
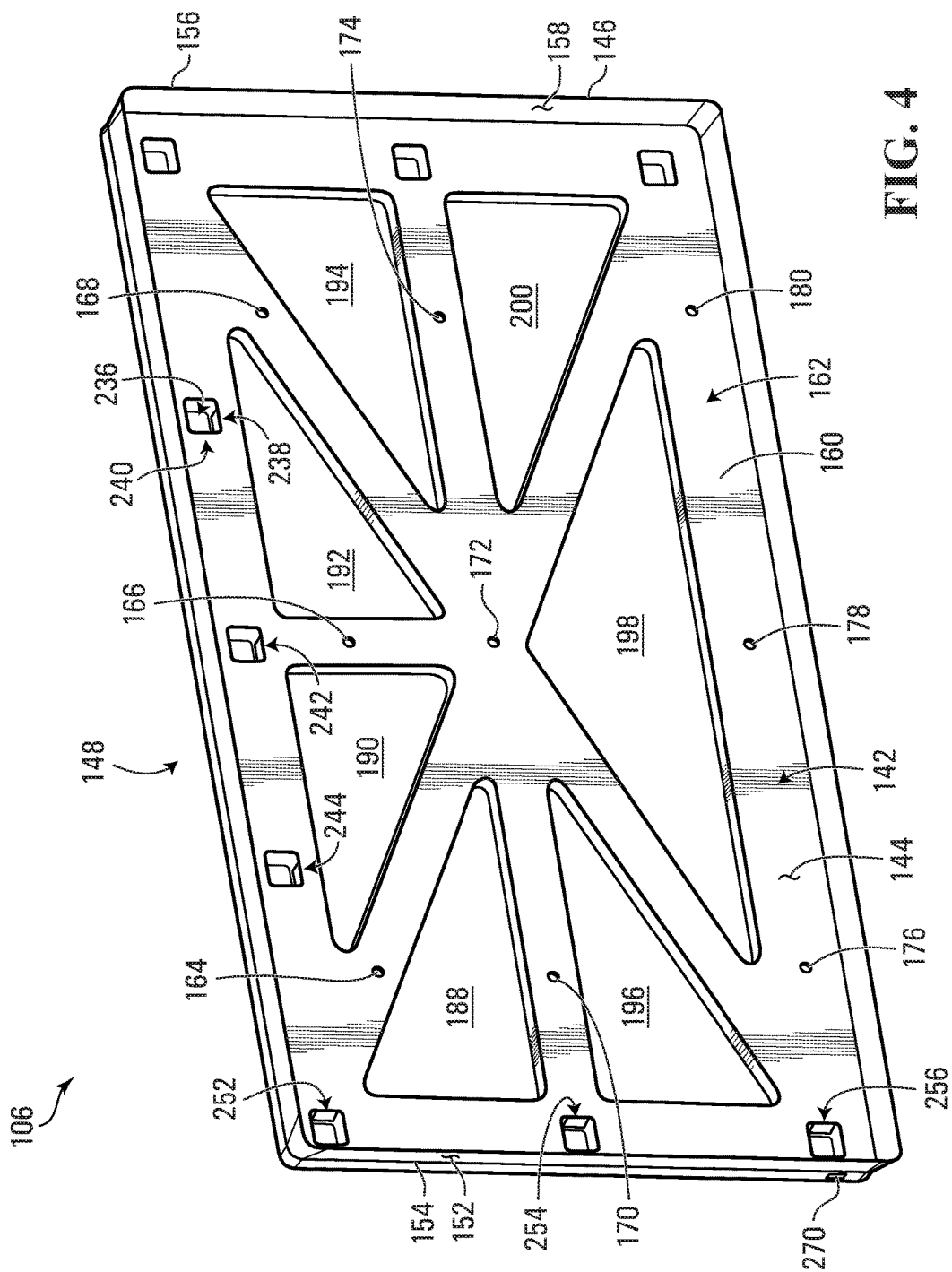
FIG. 4 is a front oblique view of a body of the headboard system of FIG. 2.
Figure 5:
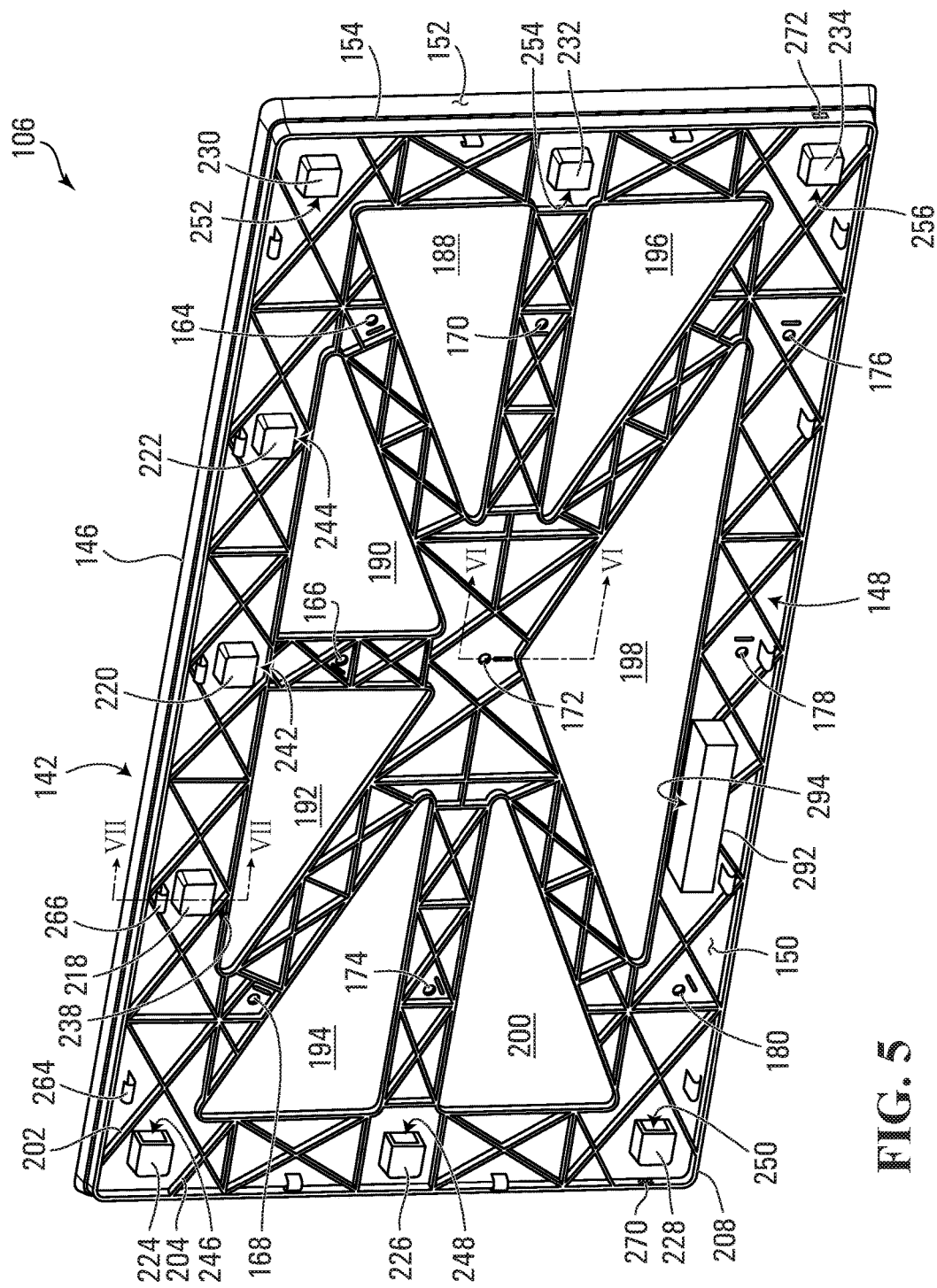
FIG. 5 is a rear oblique view of the body of FIG. 4.

Referring to FIGS. 2, 4, and 5, the body 106 has a front side shown generally at 142 and having a front surface 144 having a perimeter 146. The body 106 also has a rear side shown generally at 148 opposite the front side 142 and having a rear surface 150. The body 106 also has an outwardly facing lateral surface 152 between the front surface 144 and the rear surface 150. Further, a connector 154 is on the body 106 continuously adjacent at least a portion of the perimeter 146 of the front surface 144. In the embodiment shown, the connector 154 is a so-called "hook side" of a hook-and-loop connector, such as the hook-loop-connector commonly known as VELCRO™ for example.

Therefore, the connector 154 (which may be referred to as "a first connector" or more generally as "a holder") on the body 106 is detachably connectable to the connector 138 (which may be referred to as "a second connector") on the decorative cover 102. In the embodiment shown, the connector 138 on the decorative cover 102 and the connector 154 on the body 106 are so-called "loop side" and "hook side" sides respectively of a hook-and-loop connector, and thus the connector 154 on the body 106 is complementary to the connector 138 on the decorative cover 102.

In alternative embodiments, the decorative cover 102 may include a "hook side" of a hook-and-loop connector and the body 106 may include a "loop side" of the hook-and-loop connector, for example. Also, although the connector 154 is on the lateral surface 152 of the body 106 in the embodiment shown, the connector 154 may be on the front surface 144 or on the rear surface 150, for example, in alternative embodiments. Thus, "adjacent the perimeter 146" in this context does not require the connector 154 to adjoin or be precisely on the perimeter 146, but rather it includes embodiments where the connector 154 is close enough to the perimeter 146 that when the connector 154 is connected to the connector 138, the decorative cover 102 appears to cover at least a portion of the front surface 144 surrounded by the perimeter 146 such that the headboard system 100 generally functions as a headboard or more generally as a decorative panel.

Further, in the embodiment shown, the connector 154 extends adjacent the entire perimeter 146 of the front surface 144. However, in alternative embodiments, the connector 154 may extend adjacent substantially the entire perimeter 146 of the front surface 144, or the connector 154 may extend adjacent at least a majority of the perimeter 146 of the front surface 144. The connector 154 may be considered to extend adjacent "substantially" the entire perimeter 146 of the front surface 144 if the connector 154 extends adjacent a sufficient portion of the perimeter 146 such that the connector 154 is connectable to the connector 138 on the decorative cover 102 such that the decorative cover 102 appears to be connected continuously on the body 106.

Still referring to FIGS. 2 and 4, the body 106 defines a projection 156 having the lateral surface 152 and an inward-facing surface 158. In the embodiment shown, the front surface 144 of the body 106 includes the inward-facing surface 158 of the projection 156, and a generally flat planar portion 160. Further, the inward-facing surface 158 is between the generally flat planar portion 160 and the lateral surface 152 of the body 106. The inward-facing surface 158 and the generally flat planar portion 160 define a recess shown generally at 162 for receiving the padding 104 between the body 106 and the decorative cover 102.

Referring to FIGS. 2, 4, and 5, the body 106 defines through-openings shown generally at 164, 166, 168, 170, 172, 174, 176, 178, and 180 in the generally flat planar portion 160 of the front surface 144 and extending between the front surface 144 and the rear surface 150. As shown in FIG. 5, on the rear side 148, the body 106 defines respective cleats proximate the through-openings 164, 166, 168, 170, 172, 174, 176, 178, and 180. For example, referring to FIG. 6, the body 106 defines a cleat 182 on the rear side 148 and proximate the through-opening 172. The cleat 182 includes a relatively wide portion shown generally at 184, and a relatively narrow portion shown generally at 186 between the relatively wide portion 184 and the rear surface 150. The cleat 182 thus permits a thread or string that is passed through the through-opening 172 to be tied around the relatively narrow portion 186 and held in position by the relatively wide portion 184.

Figure 6:
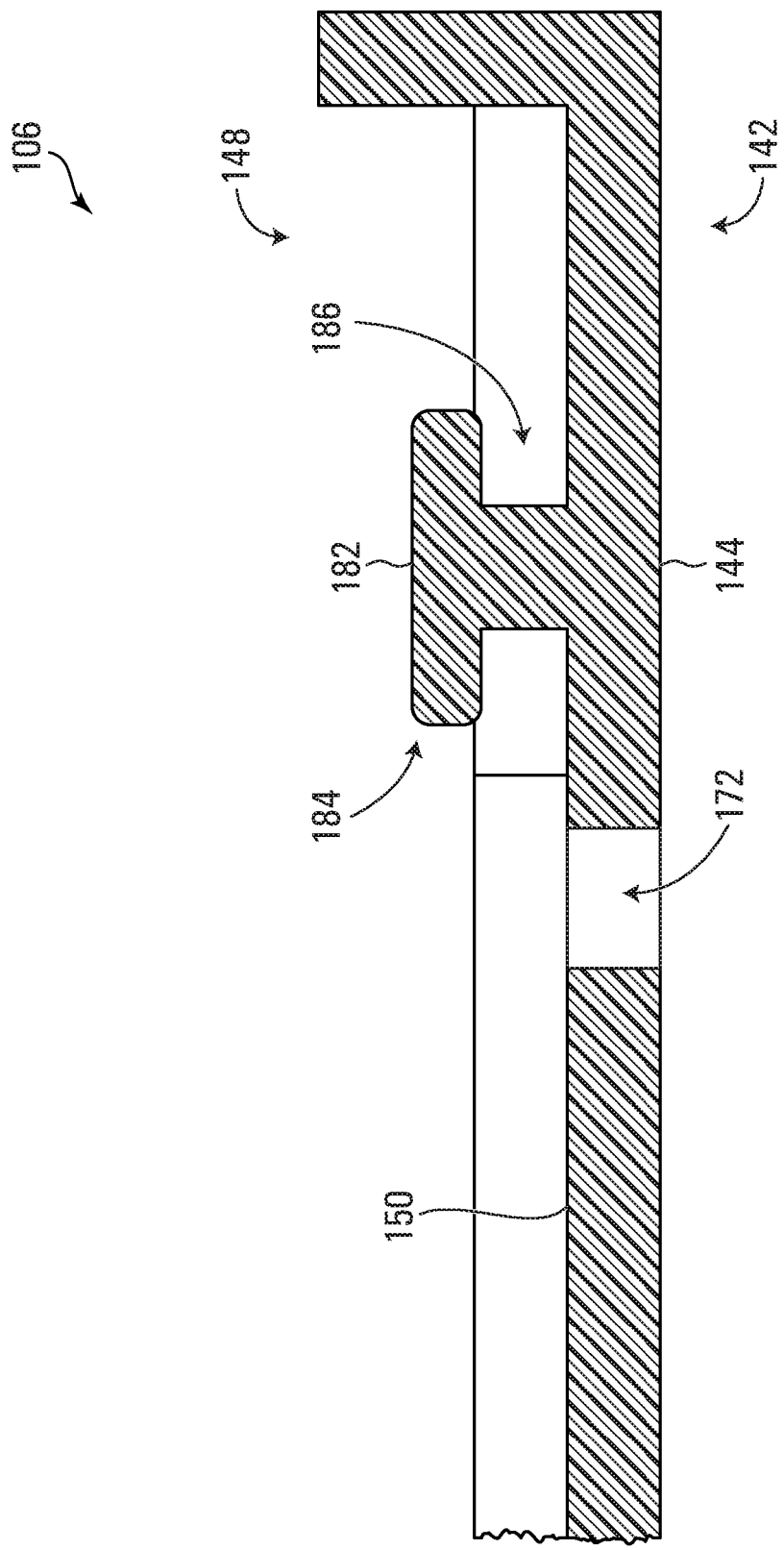
FIG. 6 is a cross-sectional view of the body of FIG. 4 along the line VI-VI in FIG. 5.

Referring to FIGS. 2, 5, and 6, the padding 104 may be received in the recess 162 of the body 106, and also in the recess 140 (also shown in FIG. 3) of the decorative cover 102. For example, using a needle (not shown), thread or string may be passed through one or more of the through-openings 164, 166, 168, 170, 172, 174, 176, 178, and 180, through the padding 104 and the decorative cover 102, through a button (not shown), and back through the decorative cover 102, the padding 104, and the through-openings of the body 106. The thread or string may then be fastened to a respective cleat, such as the cleat 182 shown in FIG. 6, for example. Therefore, the through-openings and respective cleats permit respective buttons (not shown) to be pulled against the decorative cover 102 and the padding 104 to compress regions of the padding 104 proximate the buttons to impart a textured appearance to the outer surface 112 of the decorative cover 102. In that example, the buttons and thread or string function as fasteners received through the through-openings, through the padding 104, and through the decorative cover 102 to compress the padding 104 in respective regions surrounding the respective fasteners.

Referring to FIGS. 2, 4, and 5, the body 106 defines additional through-openings 188, 190, 192, 194, 196, 198, and 200 extending between the front surface 144 and the rear surface 150. Such additional through-openings in some embodiments may reduce weight and production cost of the body 106. In alternative embodiments, the through-openings 188, 190, 192, 194, 196, 198, and 200 may be omitted or may have different shapes, or may alternatively be closed with a thin film of thermoplastic material (not shown). Such a thin film of thermoplastic material in some embodiments may protect padding (such as the padding 104 shown in FIG. 2, for example) by preventing such padding from passing through the through-openings 188, 190, 192, 194, 196, 198, and 200, or by preventing objects that may damage the padding from passing through the through-openings 188, 190, 192, 194, 196, 198, and 200.

Referring to FIG. 5, on the rear side 148, the body 106 in the embodiment shown also defines a plurality of structural ribs, such as illustrative structural ribs 202 and 204 to impart additional strength to the body 106.

Figure 7:
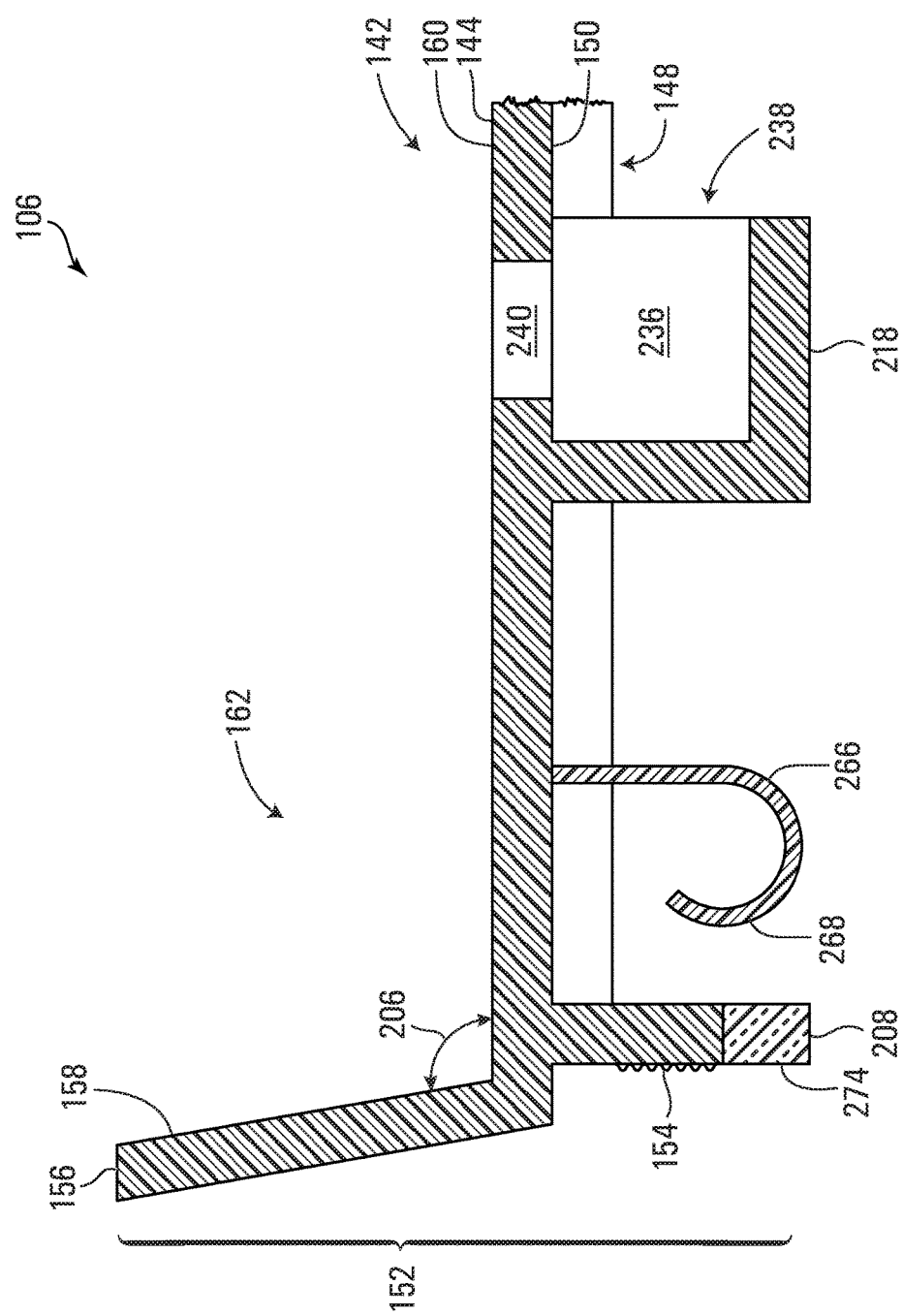
FIG. 7 is a cross-sectional view of the body of FIG. 4 along the line VII-VII in FIG. 5.

Referring to FIG. 7, in the embodiment shown, the projection 156 extends at an oblique angle 206 from the generally flat planar portion 160 of the body 106, and the body 106 also defines a projection 208 on the rear side 148 extending generally perpendicularly from the generally flat planar portion 160. In the embodiment shown, the connector 154 is on the projection 208, and the lateral surface 152 is on the projection 156 and 208. However, in alternative embodiments, the connector 154 may be on the projection 156 or, as indicated above, on the front surface 144 or on the rear surface 150.

Figure 8:
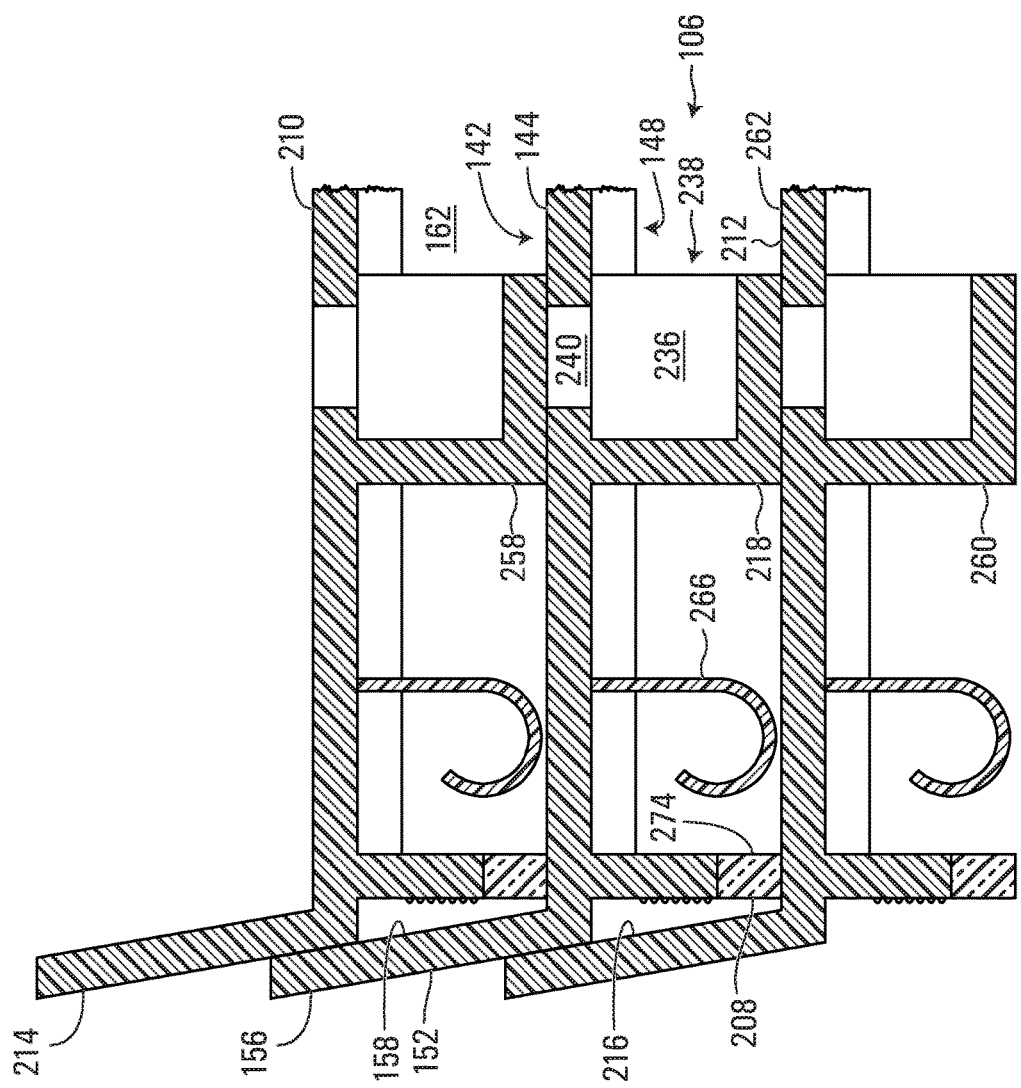
FIG. 8 is a cross-sectional view of an illustrative system of bodies including the cross-sectional view of FIG. 7.

Referring to FIG. 8, the body 106 is stackable against an adjacent similar body 210 on the front side 142 of the body 106, and against an adjacent similar body 212 on the rear side 148 of the body 106. In the embodiment shown, the adjacent similar body 210 has a lateral surface 214 that is substantially the same as the lateral surface 152 of the body 106, and the lateral surfaces 152 and 214 are positioned such that a portion of the lateral surface 214 of the adjacent similar body 210 contacts a portion of the inward-facing surface 158 of the body 106 when the adjacent similar body 210 is received in the recess 162 of the body 106 and stacked against the front side 142. Further, the adjacent similar body 212 has an inward-facing surface 216 that is substantially the same as the inward-facing surface 158 of the body 106, and at least a portion of the lateral surface 152 of the body 106 contacts at least a portion of the inward-facing surface 216 of the adjacent similar body 212 when the adjacent similar body 212 is stacked against the rear side 148 of the body 106.

Referring back to FIG. 5, the body 106 defines additional projections 218, 220, 222, 224, 226, 228, 230, 232, and 234 on the rear side 148. Referring back to FIG. 7, the projection 218 defines a cavity 236 and an opening shown generally at 238 on the rear side 148 of the body 106 and in communication with the cavity 236. The body 106 also defines an opening 240 extending between the front surface 144 of the body 106 and the cavity 236. Referring back to FIG. 5, the projections 220, 222, 224, 226, 228, 230, 232, and 234 are substantially the same as the projection 218 and define respective openings shown generally at 242, 244, 246, 248, 250, 252, 254, and 256 that are substantially the same as the opening 238. In general, the openings 238, 242, 244, 246, 248, 250, 252, 254, and 256 face inwardly from respective cavities in the respective projections.

Referring back to FIG. 8, the adjacent similar bodies 210 and 212 have respective projections 258 and 260 that are substantially the same as the projection 218. When the adjacent similar body 210 is stacked against the front side 142 of the body 106, the projection 258 of the adjacent similar body 210 contacts the front surface 144 of the body 106, and when the adjacent similar body 212 is stacked against the rear side 148 of the body 106, the projection 218 contacts a front surface 262 of the adjacent similar body 212 that is substantially the same as the front surface 144 of the body 106. Referring to FIGS. 5 and 8, the projections 218, 220, 222, 224, 226, 228, 230, 232, 234, 258, and 260 in some embodiments may thus increase contact between stacked bodies such as the stacked bodies 106, 210, and 212 as illustrated in FIG. 8, for example, and such embodiments may thus have added stability in a stacked system of bodies, such as the stacked system shown in FIG. 8 for example.

Referring back to FIG. 5, on the rear side 148, the body 106 also has a plurality of clips, such as illustrative clips 264 and 266, proximate the projection 208. Referring back to FIG. 7, the clip 266 includes a deformable curled portion 268 for detachably receiving a light source (not shown) such as a light string of light-emitting diodes ("LEDs"), for example. Thus, referring back to FIG. 5, the plurality of clips shown proximate the projection 208 function as a light source connector to connect such a light string to the body 106 substantially around a perimeter of the rear surface 150 of the body 106. Alternative connectors for the light source may include tape, for example.

Figure 9:
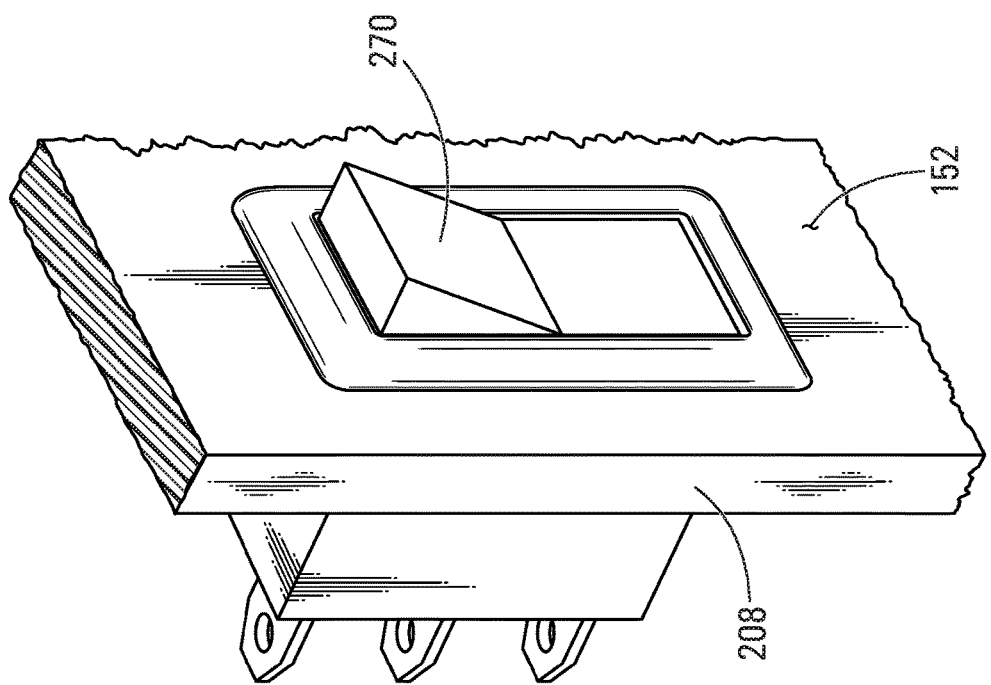
FIG. 9 is an oblique view of an electrical switch on the body of FIG. 4.

Still referring to FIG. 5, electrical switches 270 and 272 are positioned on the projection 208 of the body 106 through the lateral surface 152. Referring to FIG. 9, the electrical switch 270 is illustrated, and the electrical switch 272 is substantially the same. The electrical switches 270 and 272 in the embodiment shown are three-way switches, and thus both can be connected to a light source (not shown) such that either electrical switch 270 or 272 can turn the light source on or off. The body 106 may also have a voltage converter (not shown) to supply an appropriate voltage to the light string of LEDs, for example.

Referring back to FIG. 7, the projection 208 in the embodiment shown includes a translucent portion 274 for transmitting light from a light source (not shown) held in the clips such as the clips 264 and 266. Alternative embodiments may include a detachable translucent cover, or alternatively the translucent portion 274 may be omitted to leave a gap in the body 106 in place of the translucent portion 274, through which light may pass. Although in the embodiment shown the only translucent portion is the translucent portion 274, in alternative embodiments other portions or substantially all of the body 106 may be translucent, in which embodiments the body 106 may be formed of a single type of thermoplastic material.

Figure 10:
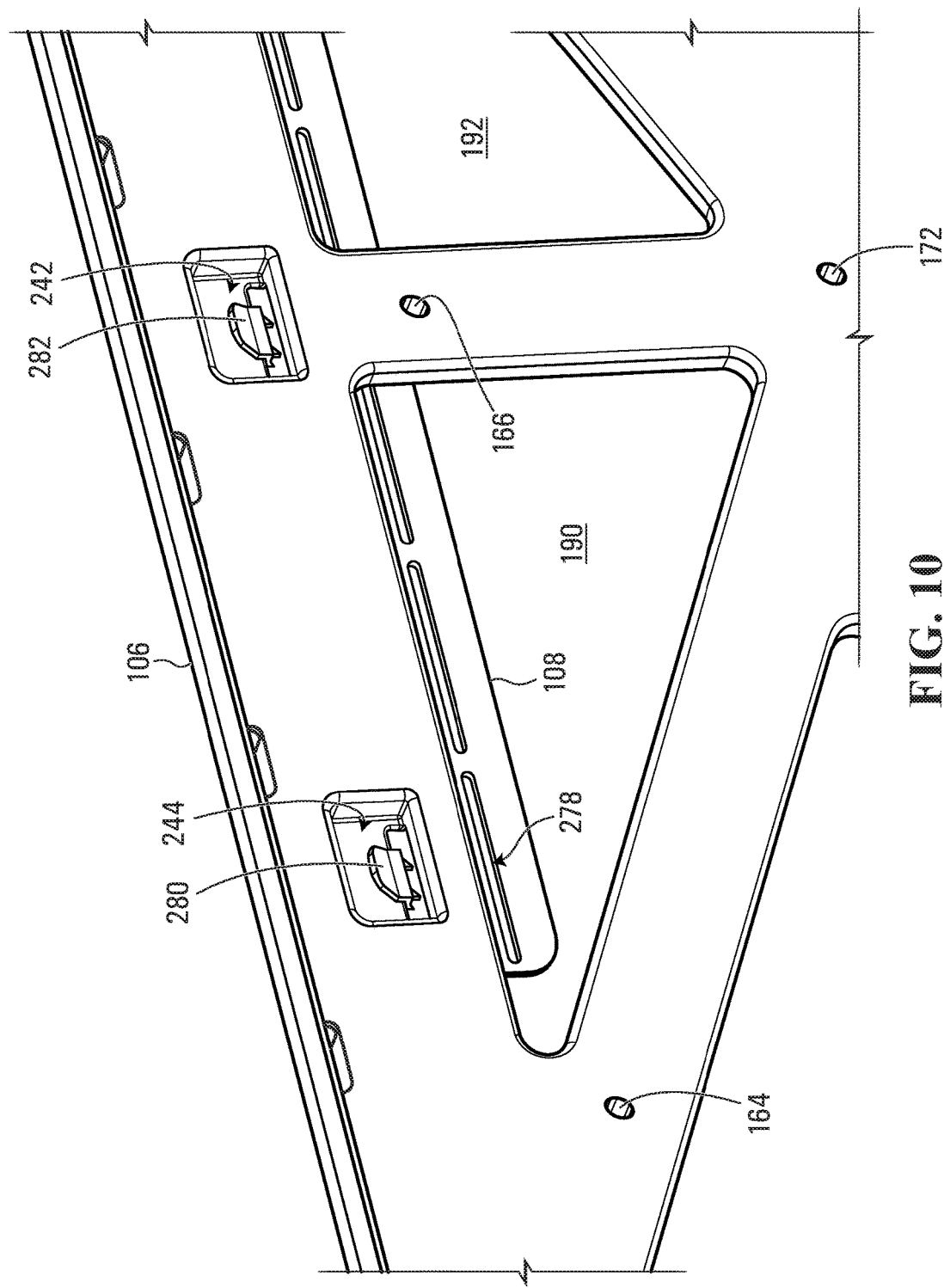
FIG. 10 is a partial oblique view of the body FIG. 4 and a cleat of the headboard system of FIG. 2.

Referring back to FIG. 2, the cleat 108 defines a plurality of through-openings, such as illustrative through-openings 276 and 278, for receiving fasteners (not shown) to mount the cleat 108 on a wall (such as the wall 88 shown in FIG. 1). Such through-openings are elongate in the embodiment shown to permit fasteners (not shown) to be attached to studs (not shown) in the wall, and to permit the cleat 108 to be slidable relative to such fasteners, which in some embodiments may enable the cleat 108 to be mounted on a wall in a position that may not be unduly restricted by positions of such studs. The cleat 108 also includes projections 280, 282, and 284 having respective upper edges 286, 288, and 290. The projections 280, 282, and 284 in the embodiment shown are spaced apart by a common spacing distance, and referring back to FIG. 5, the openings 238, 242, and 244, the openings 246, 248, and 250, and the openings 252, 254, and 256 are spaced apart by the same spacing distance. Therefore, in one embodiment, the openings 238, 242, and 244 may receive the projections 284, 282, and 280 respectively to mount the body 106 on the wall (such as the wall 88 shown in FIG. 1) to which the cleat 108 may be mounted. For example, FIG. 10 illustrates the projections 280 and 282 received in the openings 244 and 242 respectively.

In some embodiments, projections such as the projections 280, 282, and 284 may function as latches that cooperate with inner surfaces of projections such as the projections 222, 220, and 218 such that the projections 280, 282, and 284 are releasably held within the projections 222, 220, and 218 respectively, and such that the projections 280, 282, and 284 may be temporarily deformed to release the body 106 from the cleat 108. The projections 280, 282, and 284 in the embodiment shown are accessible from the front side 142 of the body 106, and may thus function as release switches to release the body 106 from the cleat 108, and in some embodiments may hold the body 106 on the cleat 108 such that the body 106 can only be released from the cleat 108 when the decorative cover 102 and padding 104 have been removed. Such releasable connection in such embodiments may further secure the body 106, padding 104, and decorative cover 102 to a wall (such as the wall 88 shown in FIG. 1).

Referring to FIGS. 2 and 5, respective spaced apart edges of the projections 218, 220, and 222 thus function as a connector on the body 106 for mounting the body 106 on a wall (such as the wall 88 shown in FIG. 1). Further, the plurality of spaced apart upper edges 286, 288, and 290 of the projections 280, 282, and 284 respectively thus function as a connector complementary to such a connector on the body 106.

Still referring to FIGS. 2 and 5, the projections 280, 282, and 284 of the cleat 108 may alternatively be received in the openings 246, 248, and 250 respectively of the projections 224, 226, and 228 respectively. The projections 224, 226, and 228 include edges that are complementary to the upper edges 286, 288, and 290 respectively of the projections 280, 282, and 284 respectively, and such edges in the projections 224, 226, and 228 are generally perpendicular, and more generally non-parallel, to substantially similar edges in the projections 218, 220, and 222. The body 106 may thus be hung in a manner perpendicular to the manner shown in FIG. 10. Further, the projections 284, 282, and 280 of the cleat 108 may also be received in the openings 252, 254, and 256 respectively of the projections 230, 232, and 234 respectively, again mounting the body 106 perpendicular to the manner shown in FIG. 10. The plurality of respective spaced apart edges of the projections 224, 226, and 228 thus also function as another connector for mounting the body 106 on a wall (such as the wall 88 shown in FIG. 1), and the plurality of respective spaced apart edges of the projections 230, 232, and 234 also function as a connector for mounting the apparatus body 106 on a wall.

Referring back to FIG. 5, the body 106 in the embodiment shown defines, on the rear side 148, a storage compartment 292 for storing objects. For example, it may be desirable to store small but valuable objects invisibly within the headboard system 100 (shown in FIG. 2). In some embodiments, the storage compartment 292 may hold one or more of buttons, a needle, and thread to impart a textured appearance to the outer surface 112 of the decorative cover 102 as described above, for example. In the embodiment shown, the storage compartment 292 is open at an opening shown generally at 294 on a top side of the storage compartment 292. However, in alternative embodiments, the storage compartment 292 may include a removable cover, for example.

Referring back to FIG. 2, in the embodiment shown, the body 106 has an inclination measuring device 296 on the front side 142. The cleat 108 also includes an inclination measuring device 298. The inclination measuring devices 296 and 298 in the embodiment shown are removable bubble levels, which in some embodiments may reveal an inclination of the body 106 and the cleat 108 respectively relative to gravitational force. Such inclination information in such embodiments may assist in positioning the cleat 108 and the body 106 level in a room, for example.

Figure 11:
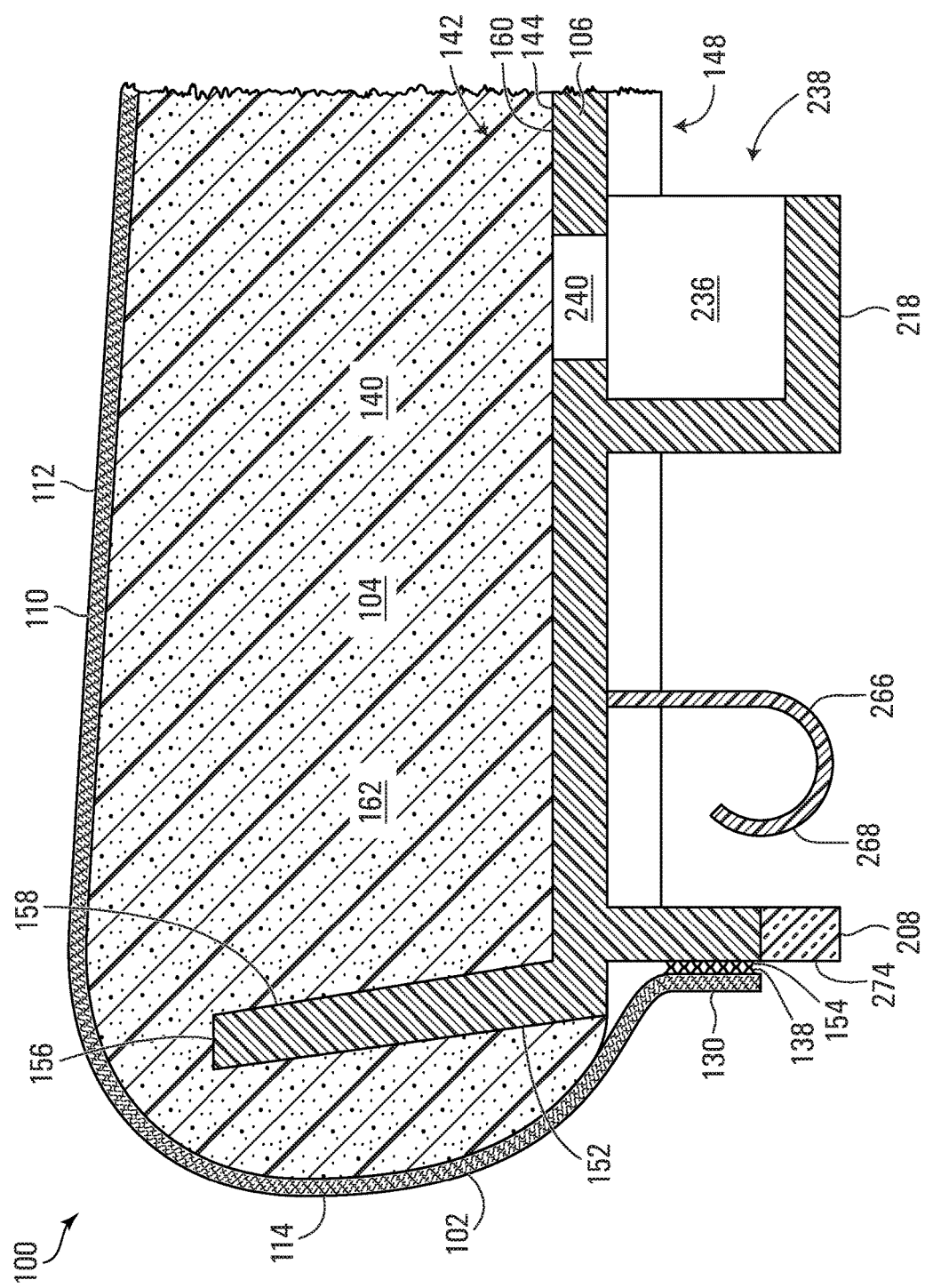
FIG. 11 is a cross-sectional view of the headboard system of FIG. 2 including the cross-sectional view of FIG. 7.

Referring to FIG. 11, the headboard system 100 is shown assembled such that the padding 104 is received in the recess 162 of the body 106 and in the recess 140 of the decorative cover 102. The lateral portions 114, 116, 118, and 120 are positioned over the lateral surface 152 of the body 106 and the connector 154 on the decorative cover 102 is detachably connected to the connector 138 on the body 106, leaving the outer surface 112 exposed to decorate a room, for example. The body 106 in the embodiment shown thus functions as an apparatus for holding the decorative cover 102, and may thus function as a headboard for a bed in some embodiments.

The hook-and-loop connectors 138 and 154 in the embodiment shown may avoid time and expense that would be involved with upholstering the decorative cover 102 to the body 106. If there is a desire to change the decorative cover 102, for example to update the outer surface 112 to reflect a new colour scheme, then the decorative cover 102 may be replaced simply by detaching the hook-and-loop connectors 138 and 154 and reattaching a connector 138 of a new decorative cover 102 to the connector 154 of the body 106.

In the embodiment shown, the body 106 and the cleat 108 are substantially thermoplastic and may be formed from high-density polyethylene or polypropylene, for example, although other thermoplastic materials, such as carbon plastic for example, may alternatively be used. The body 106 and the cleat 108 may include materials that are not thermoplastic, such as the electrical switches 270 and 272 and the inclination measuring devices 296 and 298 for example, but still be "substantially" thermoplastic. In general, a "substantially" thermoplastic body may include principal structural elements that may be formed in a mold, which may permit relatively inexpensive production of a large number of such bodies, but such a "substantially" thermoplastic body may also include elements that are not thermoplastic, such as elements of the electrical switches 270 and 272 and elements of the inclination measuring devices 296 and 298 for example. The body 106 and the cleat 108 may be made from any commonly available thermoplastic material, which may include an additive such as an additive known as ECOPURE™ available from Bio-Tec Environmental, LLC of Albuquerque, N. Mex., for example. Alternative embodiments may include other materials, which may not be thermoplastic in some embodiments.

If the headboard system 100 becomes infested with bedbugs, for example, then the decorative cover 102 and the padding 104 may be removed from the body 106 and either discarded or cleaned and replaced. For example, to kill bedbugs, the decorative cover 102 may be laundered and the padding 104 may be simply left in storage for a sufficient period of time, among other possibilities. Further, the body 106 is substantially thermoplastic and thus may be readily cleaned, and a new or cleaned decorative cover 102 and new or cleaned padding 104 may be installed on the cleaned body 106, which in some embodiments may avoid waste, expense, and environmental damage of replacing entire headboards. Such reduced waste and expense may be particularly advantageous in large institutions such as hotels for example, where responding to bedbug infestations can be very costly. Further, if it is desired to change an appearance of the decorative cover 102 or to change the padding 104, for example, then only those components need be replaced, which may reduce costs to change decor or padding material in one or more rooms or in an entire hotel, for example.

More generally, the headboard system 100 may be more hygienic than known headboards, such as upholstered headboards for example, because the substantially thermoplastic body 106 in some embodiments may be sanitized or otherwise cleaned, and the decorative cover 102 and the padding 104 may be removed, cleaned, and replaced, whereas similar components in upholstered headboards, for example, generally cannot be reused and must be discarded once removed. Therefore, some embodiments of a substantially thermoplastic body having any holder for holding a decorative cover in a headboard may be advantageous over many known headboards.

Further, one or both of the body 106 and the cleat 108 may include diatomaceous earth incorporated therein. In one embodiment, diatomaceous earth is incorporated in the body 106 by adding the diatomaceous earth to the thermoplastic material of the body 106 when the thermoplastic material is in a liquid phase before the thermoplastic material is injected into a mold. In one embodiment, about 30% by weight of the body 106 is diatomaceous earth. Further, additional diatomaceous earth may be adhered to the outwardly facing lateral surface 152 or other surfaces of the body 106. In some experiments, it has been found that bodies including diatomaceous earth in that manner effectively kill bedbugs that are in proximity to such a body. In one such experiment, such a body continued to cause death to bedbugs for at least one year after the body was manufactured. Therefore, such materials may further prevent or reduce bedbug infestations, which can be very costly in large institutions such as hotels, for example.

The diatomaceous earth in some embodiments may include CELATOM™ MN-51, which is available from EP Minerals, LLC of 9785 Gateway Drive, Suite 1000, Reno, Nev., United States of America, and which may be heat-treated or flash dried at about 900° F. (about 480° C.) or at other temperatures, for example. In one embodiment, flash drying diatomaceous earth involves heating the diatomaceous earth at about 900° F. (about 480° C.) for about 15 seconds. It is believed that such heat treatment or flash drying may change the characteristics of the diatomaceous earth to be more abrasive and thus more damaging to animal exoskeletons, or more particularly to bedbug exoskeletons, and that such heat treatment or flash drying may also dry out the diatomaceous earth, thereby making the diatomaceous earth more absorbent to dehydrate and kill an animal such as bedbug and potentially more effective in various embodiments including the various embodiments described herein.

The diatomaceous earth known as CELATOM™ MN-51 may be particularly effective in some embodiments, and such diatomaceous earth is believed to have the following properties.

TABLE 1

Properties of CELATOM ™ MN-51.

| | |
|---|---|
| Structure | Natural |
| Colour | Beige |
| G.E. Brightness | 75 |
| Sieve Analysis (Tyler) | 6.5 |
| % +325 Mesh (>44 microns) | |
| Median Particle Diameter (microns) | 15.0 |
| pH (10% slurry) | 7.5 |
| Free Moisture | |
| (Maximum % $H_2O$) | Less than 5.0 |
| (Typical % $H_2O$) | 3.0 |
| | (lb/ft³)   (g/l) |
| Density | |
| Wet Bulk | 24        385 |
| Dry Bulk | 11        176 |
| Specific Gravity | 2.00 |
| Refractive Index | 1.46 |
| Oil Absorption (ASTM F 726-81) % by weight | 150 |
| Water Absorption (ASTM F 726-81) % by weight | 165 |
| Chemical Analysis | |
| $SiO_2$ | 73.6% |
| $Al_2O_3$ | 7.8% |
| $Fe_2O_3$ | 1.8% |
| CaO | 5.6% |
| MgO | 0.3% |
| Other Oxides | 2.3% |
| Loss on Ignition | 5.5% |

In an alternative embodiment, the diatomaceous earth may include diatomaceous earth known as CELATOM™ MN-53, which is also available from EP Minerals, LLC of 9785 Gateway Drive, Suite 1000, Reno, Nev., United States of America. The diatomaceous earth known as CELATOM™ MN-53 is believed to have the following properties.

TABLE 2

Properties of CELATOM ™ MN-53.

| | |
|---|---|
| Structure | Natural |
| Colour | Beige |
| G.E. Brightness | 65 |
| Sieve Analysis (Tyler) | 5.0 |
| % +325 Mesh (>44 microns) | |
| Median Particle Diameter (microns) | 14.0 |
| pH (10% slurry) | 7.0 |
| Free Moisture | |
| (Maximum % $H_2O$) | Less than 5.0 |
| (Typical % $H_2O$) | 3.0 |
| | (lb/ft³)   (g/l) |
| Density | |
| Wet Bulk | 31        500 |
| Dry Bulk | 11        175 |
| Specific Gravity | 2.00 |
| Refractive Index | 1.46 |
| Oil Absorption (ASTM F 726-81) % by weight | 150 |
| Water Absorption (ASTM F 726-81) % by weight | 165 |
| Chemical Analysis | |

TABLE 2-continued

Properties of CELATOM ™ MN-53.

| | |
|---|---|
| $SiO_2$ | 83.7% |
| $Al_2O_3$ | 5.6% |
| $Fe_2O_3$ | 2.3% |
| CaO | 0.9% |
| MgO | 0.3% |
| Other Oxides | 1.9% |
| Loss on Ignition | 5.0% |

In one experiment on Jun. 23, 2011, small plastic Petri dishes available from Gelman Sciences™, each about 5.0 centimeters ("cm") or about 2.0 inches in diameter, were used in bioassays. A small opening of about 1.5 cm (or about 0.6 inches) in diameter was cut in the lid and closed with a piece of gauze to allow air for bedbug breathing. The Petri dishes were lined with a filter paper about 4.25 cm (or about 1.7 inches) in diameter. Diatomaceous earth was weighed and spread uniformly over the filter paper with forceps. Ten adult field-collected bedbugs were introduced in each of the Petri dishes, and the lids were placed over them to prevent their escape. Petri dishes were transferred in a plastic box lined with paper towels sprayed with water to maintain humidity in the box. Experiments were conducted at room temperature, and mortality was noted 24, 48, 72, and 96 hours after the bedbugs were introduced into of the Petri dishes. Four concentrations, between about 0.5 and about 2.0 milligrams ("mg"), were used to calculate a lowest lethal concentration sufficient to kill 50% of the bedbugs ("$LC_{50}$") of each product. There was a single replication of 10 bedbugs each.

Tables 3 and 4 below show mortality data from the Jun. 23, 2011 experiment, where L refers to a number of bedbugs still living after a corresponding time given in the tables, and D refers to a number that died after the time given.

TABLE 3

Toxicity of adult bedbugs to CELATOM ™ MN-51.

| | Amount of CELATOM ™ MN-51 | | | | | | | |
|---|---|---|---|---|---|---|---|---|
| | 2.0 mg | | 1.0 mg | | 0.8 mg | | 0.5 mg | |
| Time (hours) | L | D | L | D | L | D | L | D |
| 48 | 0 | 10 | 3 | 7 | 4 | 6 | 5 | 5 |
| 72 | | | 0 | 3 | 0 | 4 | 0 | 5 |

TABLE 4

Toxicity of adult bedbugs to CELATOM ™ MN-53.

| | Amount of CELATOM ™ MN-53 | | | | | | | |
|---|---|---|---|---|---|---|---|---|
| | 2.0 mg | | 1.0 mg | | 0.8 mg | | 0.5 mg | |
| Time (hours) | L | D | L | D | L | D | L | D |
| 48 | 6 | 4 | 9 | 1 | 7 | 3 | 8 | 2 |
| 72 | 6 | 4 | 9 | 1 | 7 | 3 | 8 | 2 |
| 96 | 0 | 6 | 4 | 6 | 6 | 4 | 7 | 3 |

All of the bedbugs died in CELATOM™ MN-51 diatomaceous earth after 48 hours. Therefore, $LC_{50}$ for CELATOM™ MN-51 was calculated for 48 hours only, and $LC_{50}$ after 48 hours for CELATOM™ MN 51 was calculated as 0.7 mg. The data after 48 hours for CELATOM™ MN-53 were not good for calculation, and therefore $LC_{50}$ for CELATOM™ MN-53 was calculated after 96 hours as 0.8 mg (0.552-1.052).

The relatively low $LC_{50}$ for CELATOM™ MN-51 suggests that CELATOM™ MN-51 may be more toxic for bedbugs than CELATOM™ MN-53, and that CELATOM™ MN-51 may be particularly effective for the control of insects, or more particularly for the control of bedbugs.

In another experiment on Feb. 1, 2012, six Petri dishes (each about 5.0 cm or about 2.0 inches in diameter) were sprayed with an aerosol including CELATOM™ MN-51, and a thin coating of the CELATOM™ MN-51 remained after drying; those six Petri dishes were used for an experimental group. An additional six Petri dishes (each 5.0 cm or about 2.0 inches in diameter) did not receive the aerosol or the diatomaceous earth; those six Petri dishes were used for a control group. Five bedbugs were introduced into each of the 12 Petri dishes, and lids were applied to prevent the bedbugs from escaping. Mortality was assessed 3, 15, 18, and 24 hours after the bedbugs were introduced into the Petri dishes, and there was no mortality in the control group. Mortality in the experimental group is shown in Table 5 below.

TABLE 5

Number of bedbugs dead from aerosol including CELATOM ™ MN-51.

| Petri dish number | Number dead after 3 hours | Number dead after 15 hours | Number dead after 18 hours | Number dead after 24 hours |
|---|---|---|---|---|
| 1 | 0 | 5 | 5 | 5 |
| 2 | 0 | 2 | 3 | 5 |
| 3 | 0 | 5 | 5 | 5 |
| 4 | 0 | 4 | 5 | 5 |
| 5 | 0 | 5 | 5 | 5 |
| 6 | 0 | 3 | 3 | 5 |
| Total | 0 | 24 | 26 | 30 |

Thus, in the Feb. 1, 2012 experiment, all of the bedbugs exposed to the aerosol including CELATOM™ MN-51 died within 24 hours, whereas none of the control group bedbugs died within 24 hours.

Another experiment on Feb. 12, 2012 involved plastic RUBBERMAID™ translucent boxes (about 73.6 cm×about 45.7 cm×about 33.7 cm, or about 29 inches×about 18 inches×about 13.3 inches), more particularly two such boxes as experimental boxes and two such boxes as control boxes. A section about 20 cm (or about 7.9 inches) wide in the center of each of the experimental boxes was sprayed with the aerosol including CELATOM™ MN-51 and allowed to dry. A piece of a field-collected sheet (about 50 cm×about 24 cm, or about 19.7 inches×about 7.9 inches) was lined on one side of each of the boxes and used as a stimulant. The sheet was collected from a home infested with bedbugs, and had eggs and many freshly fed bedbugs, but the bedbugs were collected from the sheet before placing pieces of the sheet into the boxes. Sides of the boxes opposite the pieces of the field-collected sheet were lined with a clean and new piece of cloth. Fifty adult bedbugs were introduced into each box on the clean cloth, and then the box was closed with a lid. The control boxes were similar to the experimental boxes but did not include the aerosol.

In all four of the boxes, the bedbugs moved from the sides of the boxes having the clean cloths to the sides of the boxes having the pieces of the field-collected sheet. There was no mortality in the control boxes after 48 hours, but after 24 hours, one of the experimental boxes had mortality of 43 of the 50 bedbugs, and the other of the experimental boxes had mortality of 45 of the 50 bedbugs. All of the bedbugs in the experimental boxes died after 48 hours. The bedbugs were found dead lying on their backs and dusted with the product from the aerosol. Therefore, it is believed that even a brief exposure as bedbugs cross an area treated with CELATOM™ MN-51 is sufficient to cause high mortality in the bedbugs.

It is also believed that when one bedbug contacts diatomaceous earth, that bedbug may spread the diatomaceous earth to other bedbugs, and therefore causing one bedbug to contact diatomaceous earth may cause death of several bedbugs. For example, in one experiment, a bedbug was allowed to contact diatomaceous earth and a fluorescent dye directly, and that bedbug was allowed to contact several other bedbugs that had not been allowed to contact the diatomaceous earth directly. It was found that many of the bedbugs that had not been allowed to contact the diatomaceous earth directly died shortly after contacting the bedbug that did contact the diatomaceous earth directly. Also, the fluorescent dye was observed on the bedbugs that died shortly after contacting the bedbug that did contact the diatomaceous earth directly, suggesting that such bedbugs came into contact with diatomaceous earth by contacting the bedbug that had contacted the diatomaceous earth directly. Therefore, it is believed that causing one bedbug to contacted diatomaceous earth directly may in some cases cause the deaths of several bedbugs.

In another experiment on Feb. 18, 2012, mortality of CELATOM™ MN-51 was compared with two commercially available insecticides, namely the insecticides known as ALPINE DUST™ and MOTHER EARTH™. The various products were weighed on a small filter paper, which was then placed in a Petri dish (about 5.0 cm or about 2 inches diameter). Bedbugs were introduced in the various Petri dishes, and mortality was assessed in each of the Petri dishes after 24 hours and after 48 hours. Four concentrations of each product were used, the concentrations ranging from 0.25 mg to 4 mg, and there were three replications of between 9 and 11 bedbugs in each replication. A probit analysis was used to calculate $LC_{50}$ and $LC_{95}$ (lowest lethal concentrations sufficient to kill 95% of the bedbugs) values and confidence intervals ("CIs") for the $LC_{50}$ and $LC_{95}$ values, as shown in Table 6 below.

TABLE 6

$LC_{50}$, $LC_{95}$, and CI for CELATOM ™ MN-51, ALPINE DUST ™, and MOTHER EARTH ™.

| Product | Time (hours) | $LC_{50}$ | CI of $LC_{50}$ | $LC_{95}$ | CI of $LC_{95}$ |
|---|---|---|---|---|---|
| CELATOM ™ MN-51 | 24 | 0.24 | 0.14-0.32 | 0.95 | 0.69-1.98 |
| ALPINE DUST ™ | 24 | 6.36 | 3.83-29.27 | 52.57 | 15.88-3366 |
| ALPINE DUST ™ | 48 | 1.72 | 1.37-2.18 | 6.6 | 4.47-13.44 |
| MOTHER EARTH ™ | 24 | 0.26 | 0.14-0.36 | 1.37 | 0.91-3.44 |

The data in Table 6 show that CELATOM™ MN-51 required lower concentrations (specifically lower $LC_{50}$ and $LC_{95}$, and lower CIs for those values) than ALPINE DUST™ and MOTHER EARTH™ in that experiment, and therefore it is believed that CELATOM™ MN-51 may generally be more effective than ALPINE DUST™ and MOTHER EARTH™ in controlling populations of bedbugs.

In general, it is believed that diatomaceous earth may damage exoskeletons of animals having exoskeletons, which damage may lead to dehydration and death of the animals. Therefore, it is believed that diatomaceous earth, and various apparatuses, kits, and systems such as those including diatomaceous earth as described herein, may be effective in the control of populations of one or more of animals having exoskeletons, arthropods, arachnids, insects, and bedbugs. Herein, "control" of an animal population may include prevention of growth or survival of such a population before discovery of the population, and also killing one or more members of such a population after discovery of the population. Diatomaceous earth is also a natural product, and in general, natural products may be preferable over other pest control products because natural products may be less harmful to humans or more generally to the environment. Animals that may desirably be killed by diatomaceous earth also include cockroaches, ants, fleas, and other pests.

Although CELATOM™ MN-51 and CELATOM™ MN-53 and other products have been discussed above, some embodiments may include other types of diatomaceous earth, which may be supplied by other suppliers. In general, such diatomaceous earth in some embodiments may be heat-treated or flash dried diatomaceous earth, such as diatomaceous earth flash dried at about 480° C. for about 15 seconds for example, or may more generally be modified diatomaceous earth. More generally, such diatomaceous earth may have one or more properties similar to one or more of the properties of CELATOM™ MN-51 or CELATOM™ MN-53 listed in Tables 1 and 2 above in order to achieve effects that may be similar to the effects of CELATOM™ MN-51 or CELATOM™ MN-53 described above.

Further, other embodiments may include products other than diatomaceous earth that may be effective to control bedbug populations or more generally as an insecticide or pesticide. For example, U.S. Pat. No. 8,101,408 describes various legume extracts, such as one or more of PA1b-related peptides, terpenoid saponins, triterpenoid saponin, soyasaponin I, soyasaponin II, soyasaponin III, soyasaponin VI, dehydrosoyasaponin I, echinocystic acid 3-glucoside, glycyrrhizic acid, hederacoside C, beta-escin, alpha-hederin, and other acetic acid precipitated insecticidal components. In various embodiments, one or both of diatomaceous earth and such legume extracts may be incorporated into thermopoastic bodies, for example by adding the diatomaceous earth, the legume extracts, or both to the thermoplastic material of the body when the thermoplastic material is in a liquid phase and before the thermoplastic material is injected into a mold.

Still referring to FIG. 11, the decorative cover 102 and the body 106 may be manufactured to have the hook-and-loop connectors 138 and 154 in predetermined positions on the decorative cover 102 and on the body 106 respectively, and such predetermined positions may be determined to impart a desired position and tension of the decorative cover 102 over the padding 104. Therefore, the decorative cover 102 may be installed with such a desired position and tension simply by aligning the connector 138 with the connector 154. Therefore, in the embodiment shown, the connector 154 on the body 106 complementary to the connector 138 on the decorative cover 102 may simplify holding the decorative cover 102 on the body 106 because a desirable position of decorative cover 102 on the body 106 may be predetermined by the respective positions of the complementary connectors 138 and 154, which may eliminate a need to position a decorative cover carefully on a frame while connecting the decorative cover to the frame. Further, in some embodiments, there is no need to stretch or deform the decorative cover 102 when installing it on the body 106.

Still further, in the embodiment shown, the connectors 138 and 154 are continuous hook-and-loop connectors, and therefore may avoid unsightly looks that can result from connecting a decorative cover only at discrete points on a frame.

Figure 12:
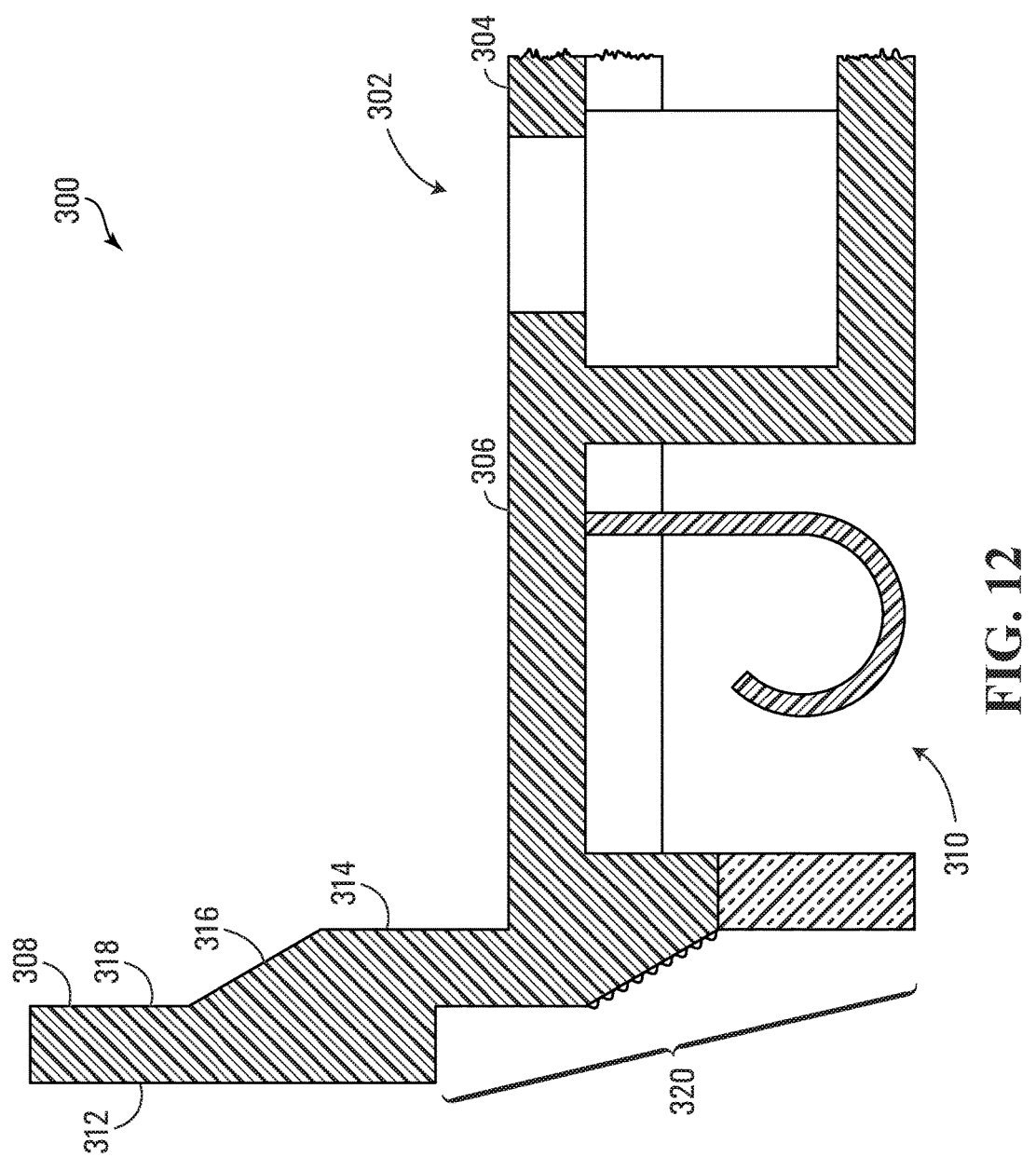
FIG. 12 is a partial cross-sectional view of another illustrative body.

Referring to FIG. 12, another illustrative body is shown generally at 300 and has a front side shown generally at 302 and having a front surface 304. The front surface 304 includes a generally flat planar portion 306 and an inward-facing portion 308. The body 300 also has a rear side shown generally at 310 opposite the front side 302, and an outwardly facing lateral surface 312. The inward facing portion 308 of the front surface 304 is therefore between the generally flat planar portion 306 and the lateral surface 312 of the body 300. The body 300 is substantially similar to the body 106 discussed above, may similarly function as an apparatus for holding a decorative cover, and may include similar materials to the body 106, although the inward-facing portion 308 includes a first portion 314 adjacent and extending generally perpendicular to the generally flat planar portion 306, a second portion 316 adjacent the first portion 314 and extending non-parallel to the first portion 314 and away from the generally flat planar portion 306, and a third portion 318 adjacent the second portion 316 and extending generally parallel to the first portion 314 and away from the generally flat planar portion 306. Also, the lateral surface 312 in the embodiment shown includes a complementary portion 320 that is generally complementary to the inward-facing portion 308.

Figure 13:
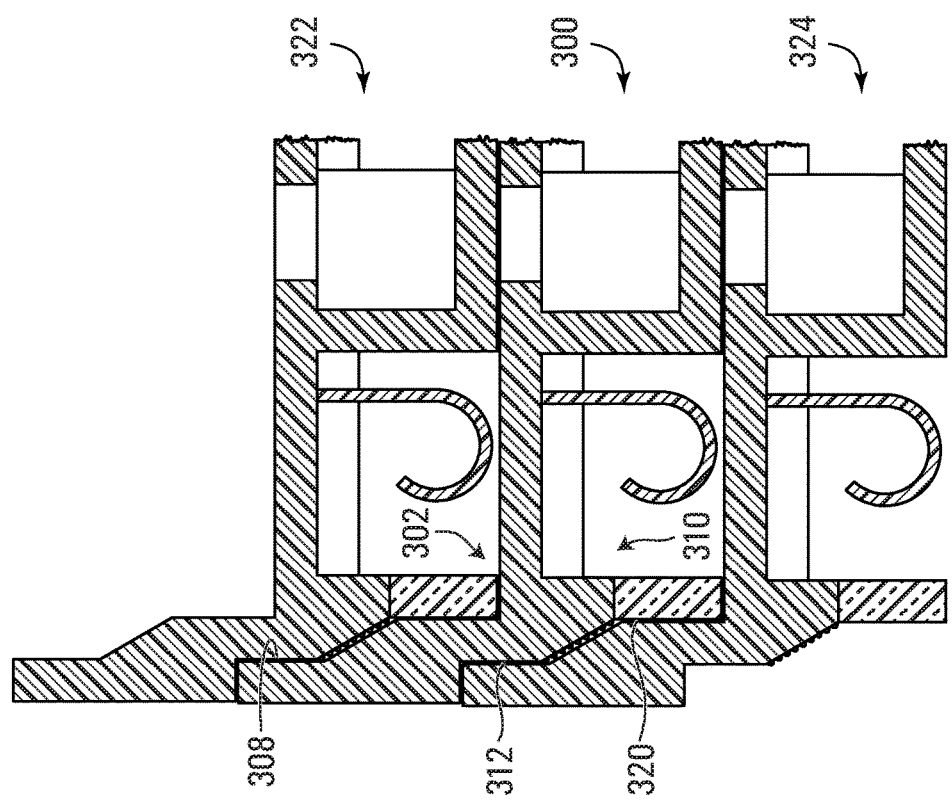
FIG. 13 is a cross-sectional view of an illustrative system of bodies including the cross-sectional view of FIG. 12.

Therefore, referring to FIG. 13, the body 300 is stackable against an adjacent similar body 322 on the front side 302 of the body 300, and against an adjacent similar body 324 on the rear side 310 of the body 300. Thus, the complementary portion 320 of the lateral surface 312 of the adjacent similar body 322 contacts the inward-facing portion 308 of the body 300 when the adjacent similar body 322 is stacked against the front side 302 of the body 300. Further, the complementary portion 320 of the lateral surface 312 of the body 300 contacts the inward-facing portion 308 of the adjacent similar body 324 when the adjacent similar body 324 is stacked against the rear side 310 of the body 300.

Figure 14:
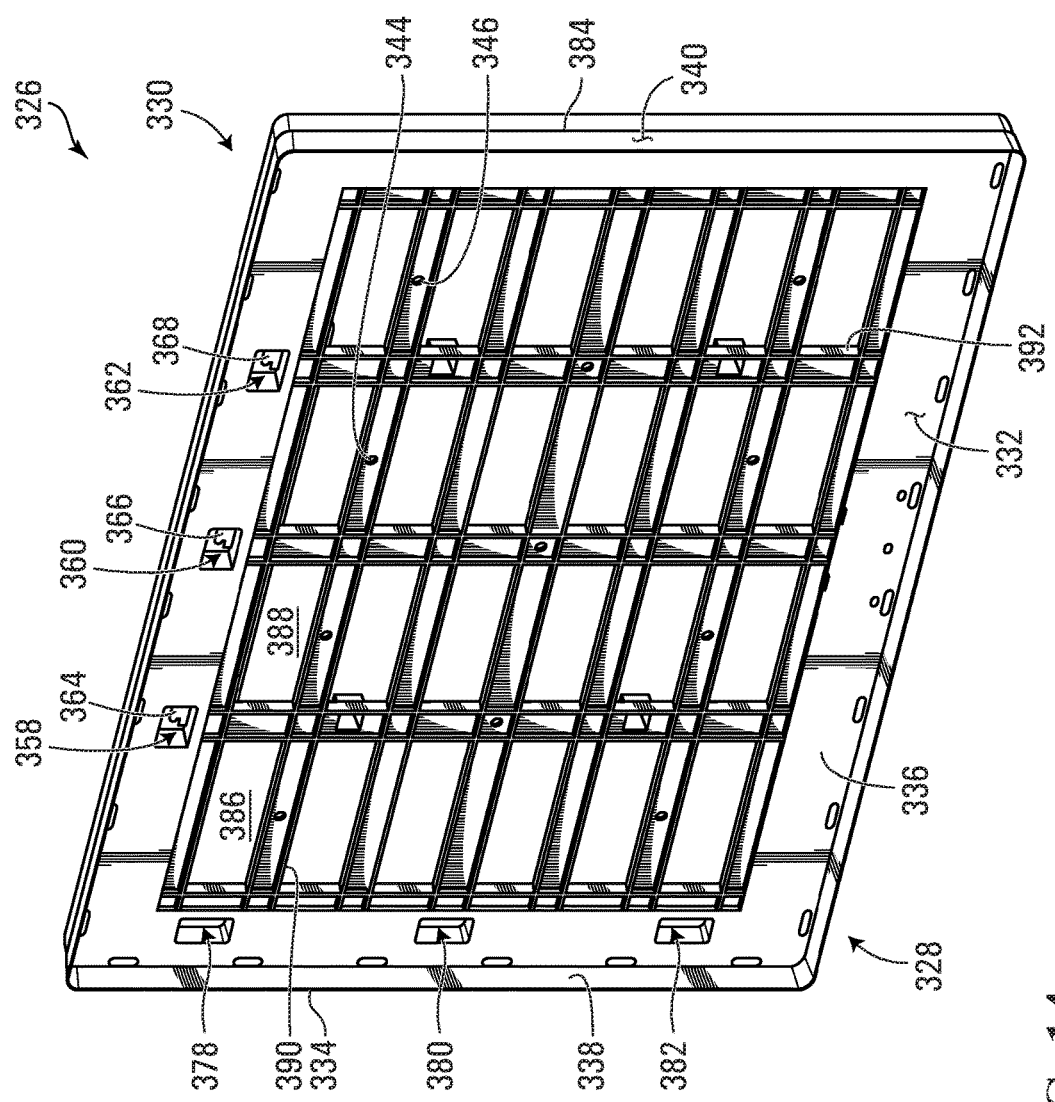
FIG. 14 is a front oblique view of another illustrative body.
Figure 15:
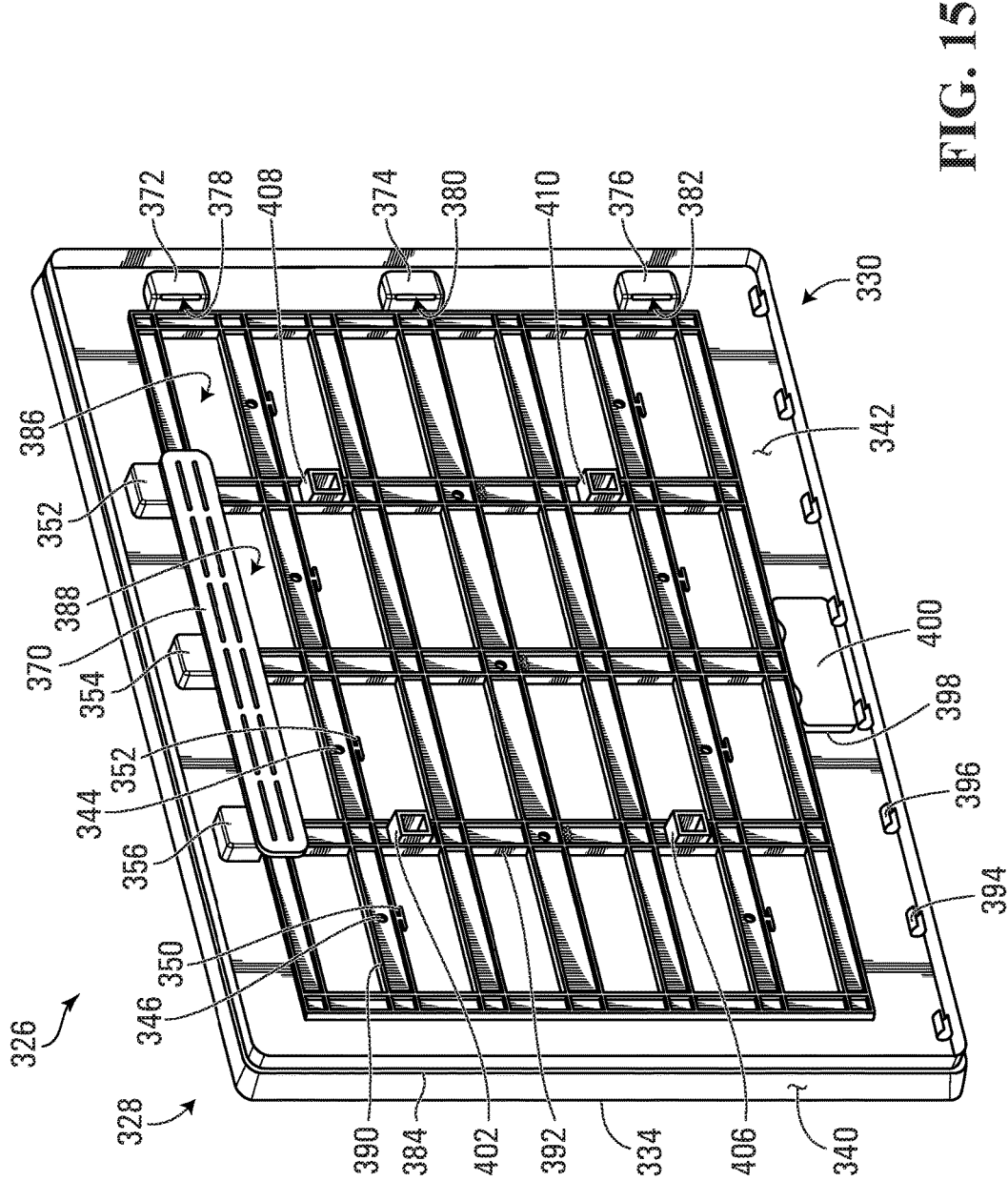
FIG. 15 is a rear oblique view of the body of FIG. 14 and of an illustrative cleat.
Figure 16:
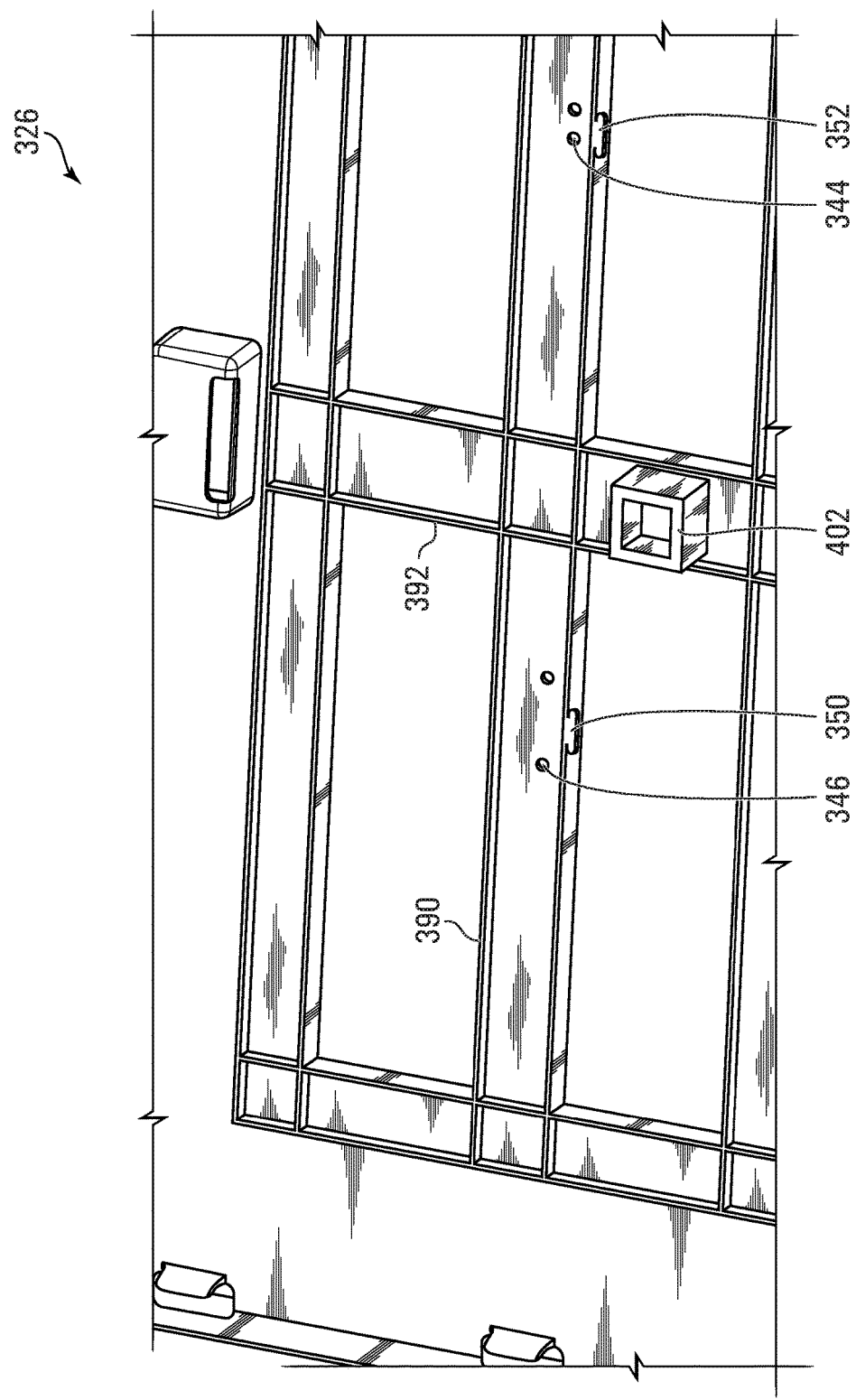
FIG. 16 is a partial rear oblique view of the body of FIG. 14.

Referring to FIGS. 14, 15, and 16, another illustrative body is shown generally at 326 and includes a front side shown generally at 328 and an opposite rear side shown generally at 330. The front side 328 has a front surface 332 having a perimeter 334, and includes a generally flat planar portion 336 and an inward-facing portion 338. The body 326 also includes an outwardly facing lateral surface 340 between the front surface 332 and a rear surface 342 on the rear side 330. The body 326 defines a plurality of through-openings such as illustrative through-openings 344 and 346 for receiving respective fasteners as discussed above with the through-opening 172 shown in FIG. 6, for example. The through-openings such as the through-opening 344 and 346 also have respective cleats 348 and 350 that are substantially the same as the cleat 182 discussed above and shown in FIG. 6. On the rear side 330, the body 326 defines projections 352, 354, and 356 having respective through-openings shown generally at 358, 360, and 362 for receiving respective projections 364, 366, and 368 of a wall-mountable cleat 370 that is substantially the same as the cleat 108 discussed above. The body 326 also defines, on the rear side 330, projections 372, 374, and 376 having respective through-openings shown generally at 378, 380, and 382 for receiving the projections 368, 366, and 364 respectively of the cleat 370. The body 326 is thus wall-mountable in a first orientation when the projections 364, 366, and 368 are received in the through-openings 358, 360, and 362 respectively, and in a second orientation perpendicular to the first orientation when the projections 364, 366, and 368 are received in the through-openings 382, 380, and 378 respectively. The spaced apart edges of the projections 364, 366, and 368 thus function as a connector, the spaced apart edges of the projections 356, 354, and 352 thus function as a connector complementary to the spaced apart edges of the projections 364, 366, and 368, and the spaced apart edges of the projections 376, 374, and 372 also function as a connector complementary to the spaced apart edges of the projections 364, 366, and 368.

The body 326 also has a connector 384 continuously adjacent the perimeter 334 of the front surface 332, and in the embodiment shown the connector 384 is on the lateral surface 340. The connector 384 is complementary to a connector such as the connector 138 on the decorative cover 102 shown in FIG. 3, and thus the body 326 also functions as an apparatus for holding a decorative cover.

The body 326 also defines additional through-openings such as illustrative through-openings 386 and 388, which may reduce a weight and manufacturing cost of the body 326. In the embodiment shown, the additional through-openings such as the through-openings 386 and 388 are generally rectangular and separated by generally linear members such as illustrative generally linear members 390 and 392, which have through-openings such as the through-openings 344 and 346 and cleats such as the cleats 348 and 350. However, in alternative embodiments, the through-openings such as the through-openings 386 and 388 may be omitted or closed by thin films of thermoplastic material (not shown) received against the front surface 332.

The body 326 also has clips such as illustrative clips 394 and 396, and such clips function as a light source connector for holding a light source (not shown), which may include a plurality of LED lights in a light string, for example. The clips such as the clips 394 and 396 are substantially the same as the clips such as the clips 264 and 266 shown in FIGS. 5 and 7 and discussed above.

Also, on the rear side 330, the body 326 defines a storage compartment 398 for storing objects. In the embodiment shown, the storage compartment 398 includes a removable cover 400. Again, in some embodiments, the storage compartment 398 may hold one or more of buttons, a needle, and thread to impart a textured appearance to the outer surface 112 of the decorative cover 102 as described above, for example.

The body 326 also includes additional projections 402, 406, 408, and 410 on the rear surface 342 to contact at least a portion of an adjacent similar apparatus when the adjacent similar apparatus is stacked against the rear side 330 of the body 326. The additional projections 402, 406, 408, and 410 in some embodiments may thus impart greater stability to a system of stacked similar bodies. The body 326, and other bodies and cleats such as those disclosed herein, may be made from materials such as those discussed above for the body 106.

Figure 25:
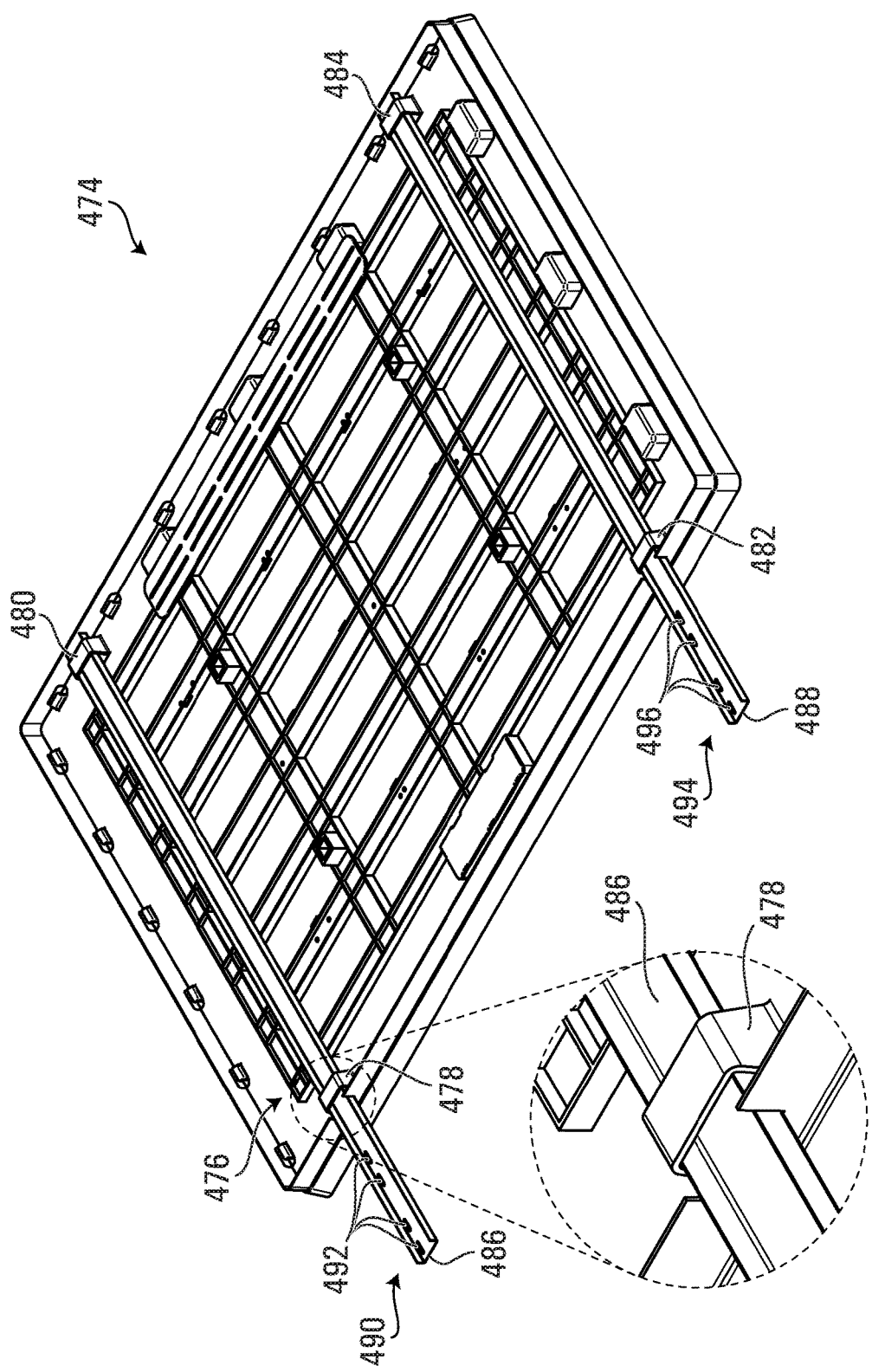
FIG. 25 is a rear oblique view of another illustrative body.

Referring to FIG. 25, another illustrative embodiment is shown generally at 474 and is similar to the body 326 shown in FIGS. 14, 15, and 16, except that on a rear side 476 of the body 474, the body 474 defines receptacles 478, 480, 482, and 484. In the embodiment shown, the receptacles 478 and 480 receive a support 486, and the receptacles 482 and 484 receive a support 488. When the support 486 is received fully in the receptacles 478 and 480, an exposed end shown generally at 490 of the support 486 has a plurality of through-openings 492 for receiving fasteners (not shown) to attach the support 490 to a bed frame (not shown). Likewise, when the support 488 is fully received in the receptacles 482 and 484, an exposed end shown generally at 494 of the support 488 defines a plurality of through-openings 496 for receiving fasteners (not shown) for attaching the support 488 to the bed frame (not shown). The receptacles 478, 480, 482, and 484 thus function as a connector for connecting the body 474 to a bed frame.

Figure 17:
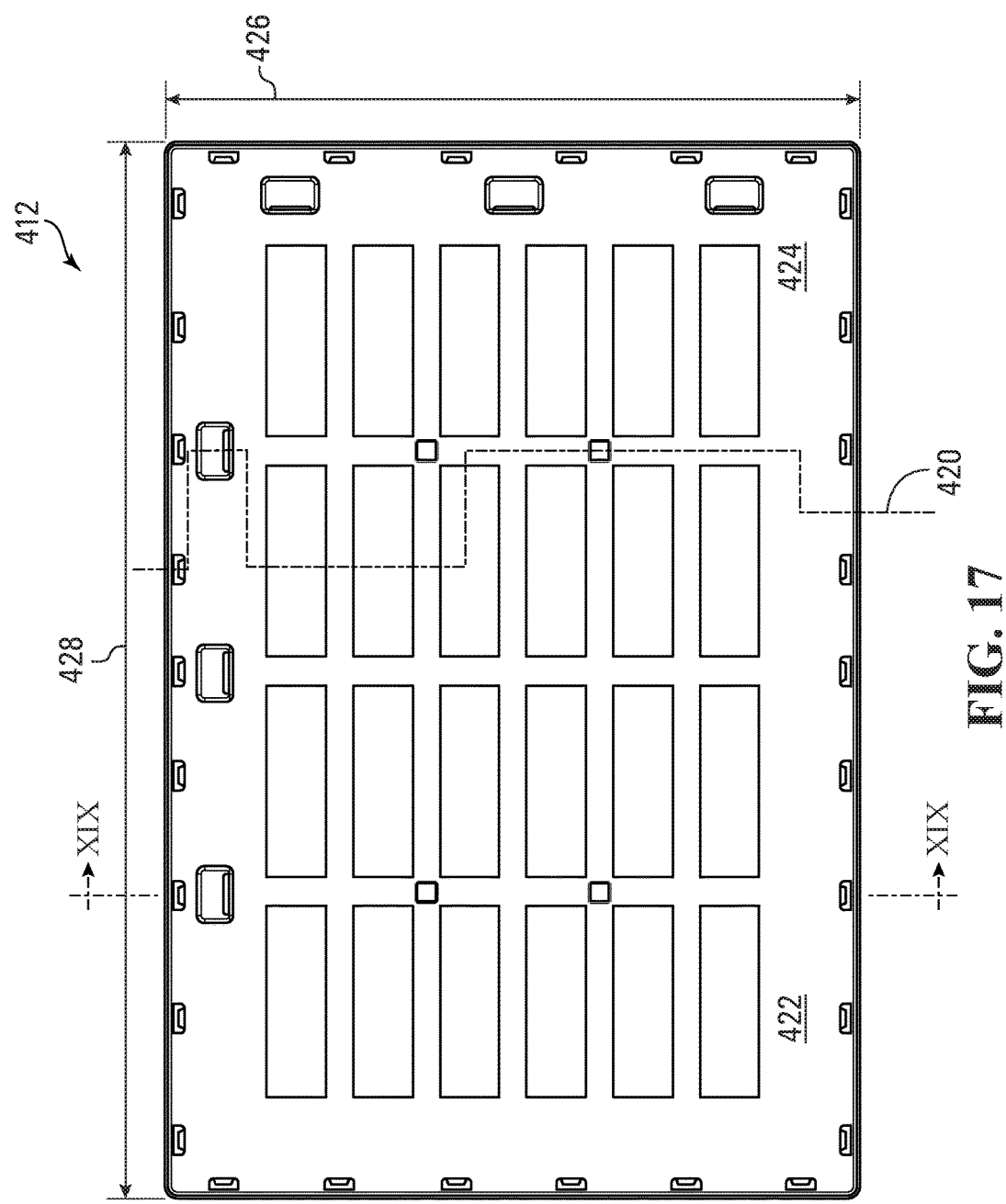
FIG. 17 is a front plan view of another illustrative body.
Figure 18:
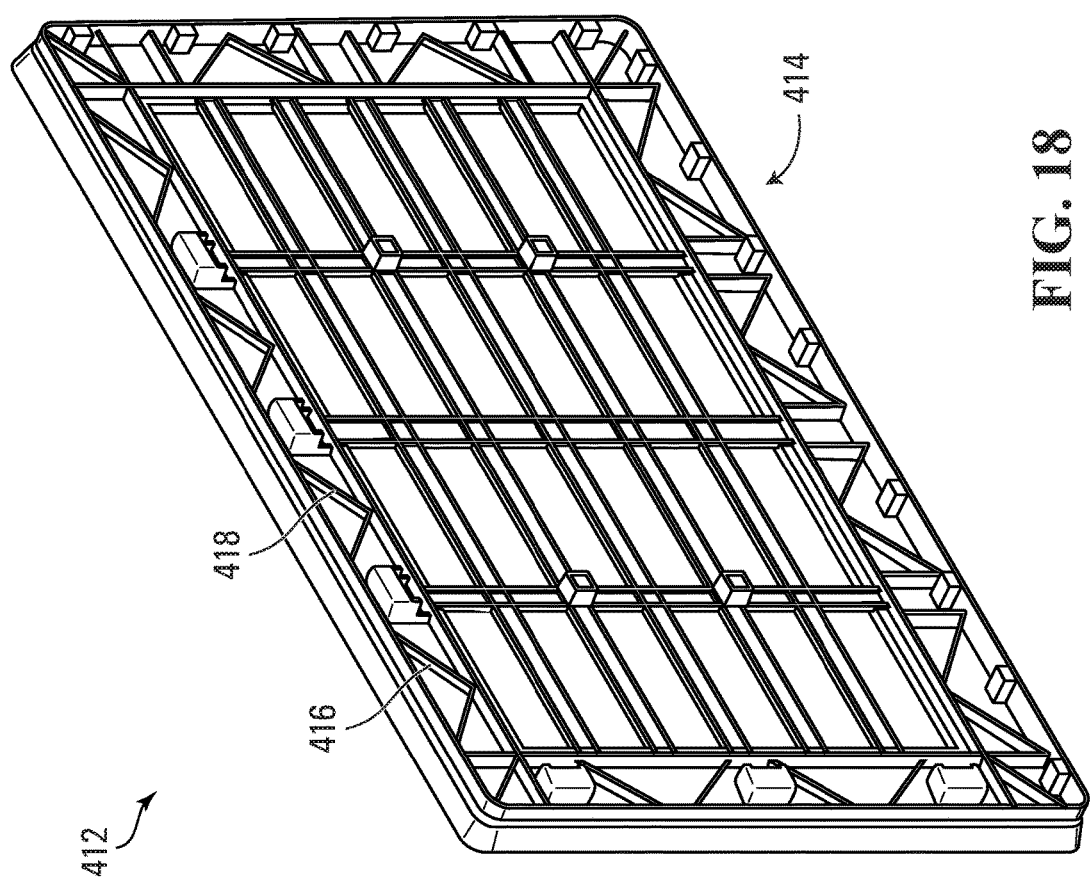
FIG. 18 is a rear oblique view of the body of FIG. 17.
Figure 19:
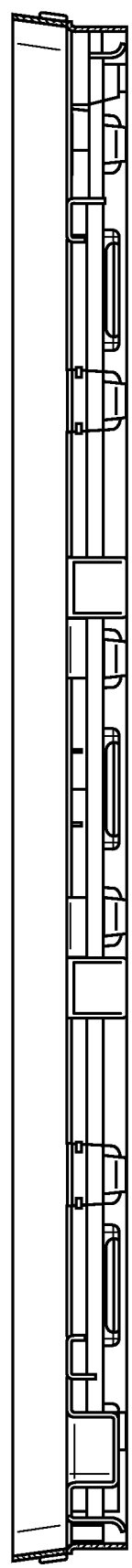
FIG. 19 is a cross-sectional view of the body of FIG. 17 along the line XIX-XIX in FIG. 17.

Referring to FIGS. 17, 18, and 19, another illustrative body is shown generally at 412 and is similar to the body 326 except that on a rear side 414 of the body 412, the body 412 includes a plurality of structural reinforcing ribs such as illustrative structural reinforcing ribs 416 and 418.

The body 412 in the embodiment shown is substantially thermoplastic and may be formed in a mold. Such molds are costly to produce, and therefore such molds are preferably adjustable in size to produce bodies similar to the body 412 but having different dimensions. For example, referring to FIG. 17, the line 420 divides the body 412 into portions 422 and 424 that may be formed by respective separate portions of a mold. Those portions of the mold may be separated, and an additional portion of the mold may be inserted therebetween to form a body similar to the body 412 but larger by having an additional portion (not shown) between the portions 422 and 424.

In the embodiment shown, the body 412 has a height 426 of about 109.2 cm (or about 43 inches), and a width 428 of about 147.3 cm (or about 58 inches). Such dimensions may be suitable for a headboard for a North American double-sized bed having a width of about 137.2 cm (or about 54 inches). However, in North America, a queen-sized bed having a width of about 152 cm (or about 60 inches) is also common, and therefore a body suitable for use as a headboard for a North American queen-sized bed may have a width of about 162.6 cm (or about 64 inches) by expanding the mold by inserting a mold expansion portion into the mold, the mold expansion portion having a width of about 15.3 cm (or about 6 inches) to cause an additional portion having a width of about 15.3 cm (or about 6 inches) to be formed in the body 412 between the portions 422 and 424. Also, some North American king-size beds have a width of about 203.2 cm (or about 80 inches), and therefore two bodies 412 may be rotated by 90° and positioned adjacent each other to have a common width of about 218.4 cm (or about 86 inches, namely about twice the height 426) and to have a common height of about 147.3 cm (or about 58 inches, namely about equal to the width 428). Therefore, with a mold expansion portion to form an additional portion between the portions 422 and 424, a single mold may produce bodies suitable for headboards of three different sizes of beds, such as North American double-, queen-, and king-sized beds for example.

In alternative embodiments, a body may include telescoping portions to permit adjustment of an overall size of the body.

Figure 20:
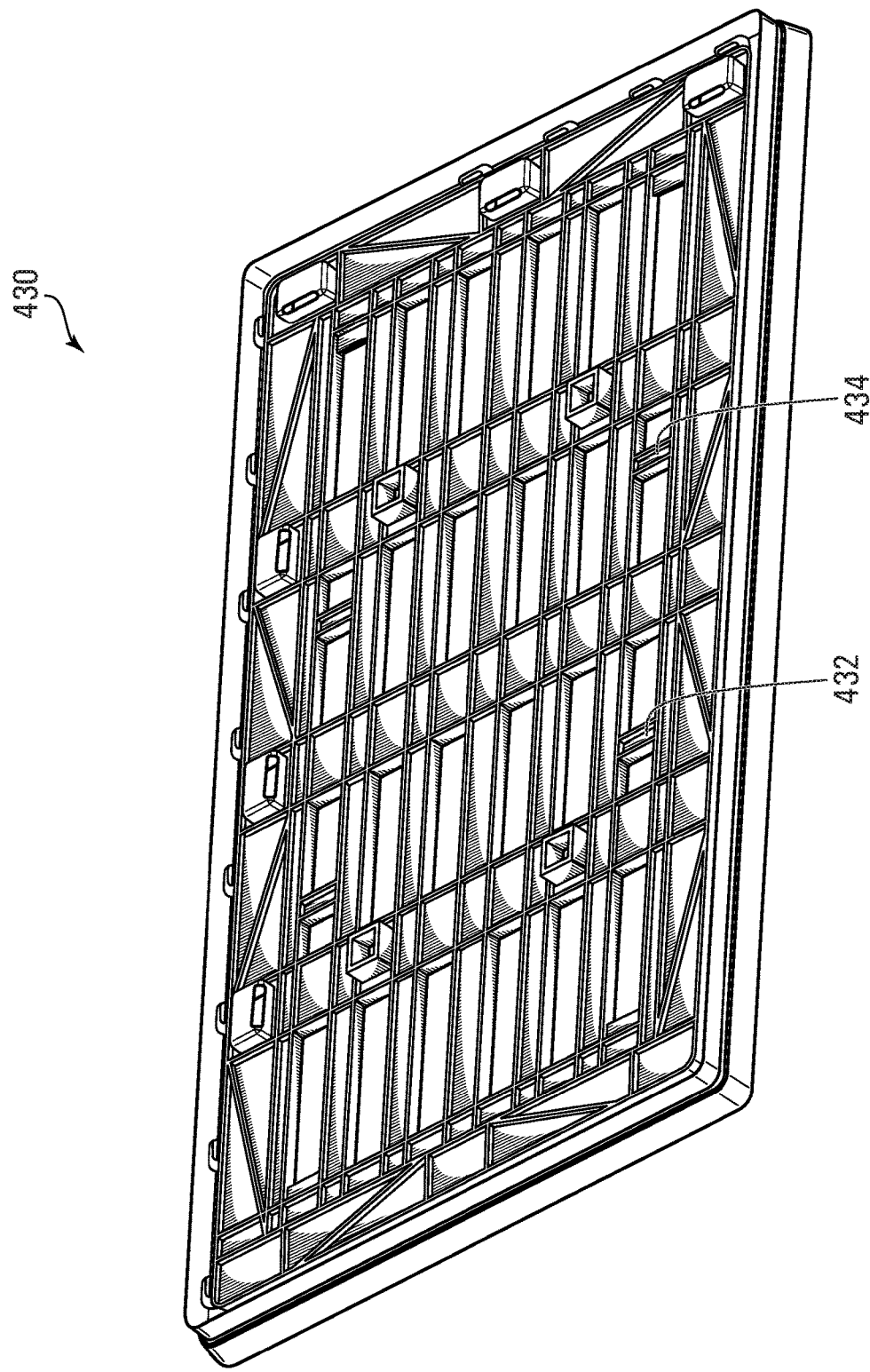
FIG. 20 is a rear oblique view of another illustrative body.

Referring to FIG. 20, another illustrative body is shown generally at 430 and is similar to the body 412 except that the body 430 includes additional generally linear members 432 and 434 for additional structural strength. The body 430 also may function as an apparatus for holding a decorative cover similar to the bodies 106, 300, 326, and 412, and may include similar materials as described above.

Figure 21:
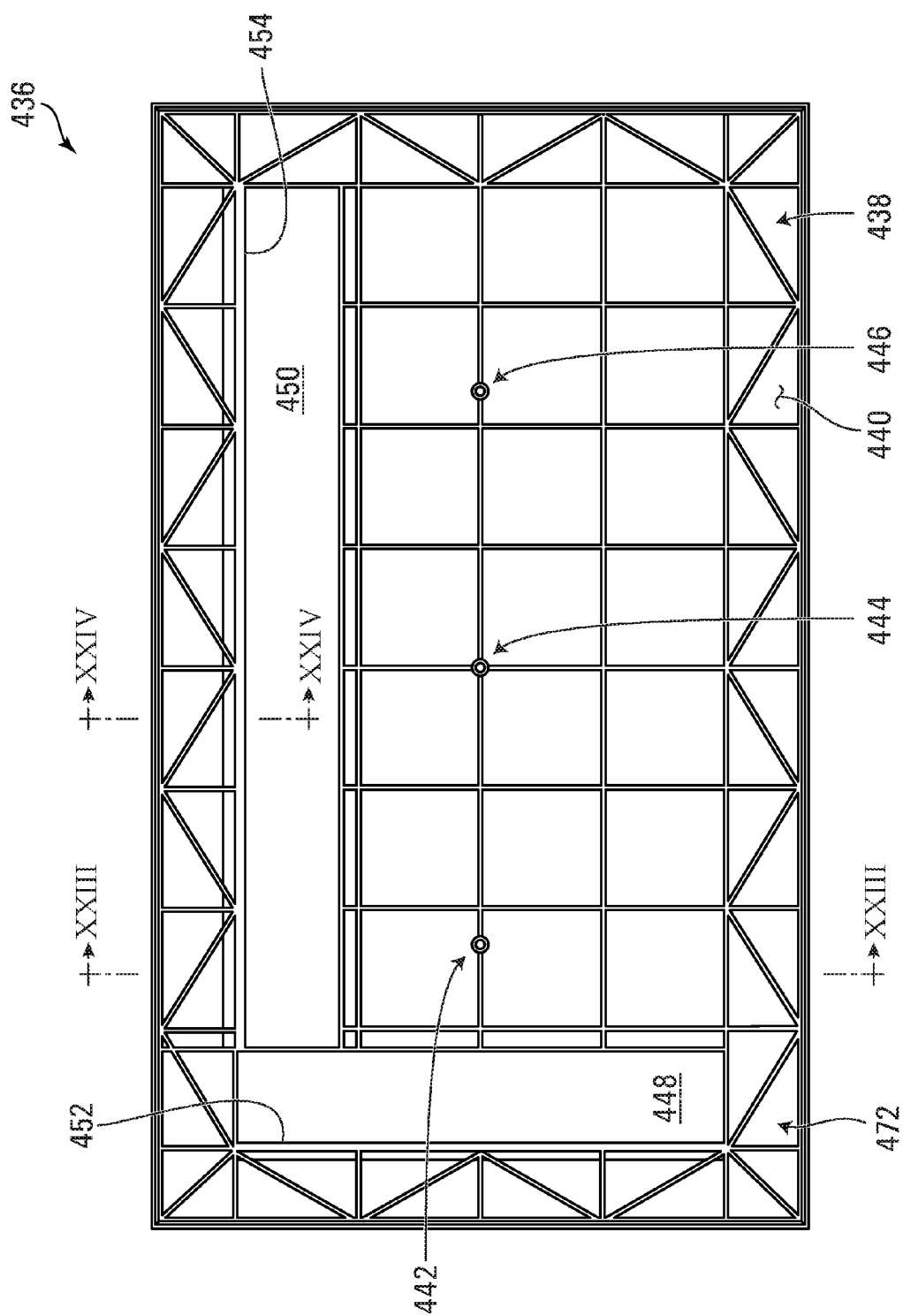
FIG. 21 is a rear plan view of another illustrative body.

Referring to FIG. 21, another illustrative body is shown generally at 436. The body 436 may function as an apparatus for holding a decorative cover similar to the bodies 106, 300,

326, 412, and 430, and may include similar materials as described above. The body 436 has a rear side shown generally at 438 and having a rear surface 440. The body 436 defines through-openings generally at 442, 444, and 446 for receiving fasteners similar to the through-opening 172 discussed above and shown in FIG. 6, for example.

The body 436 also defines through-openings 448 and 450. The through-opening 448 is adjacent a bevelled edge 452, and the through-opening 450 is adjacent a bevelled edge 454. The bevelled edges 452 and 454 are connectors complementary to a French cleat to mount the body 436 on a wall (such as the wall 88 shown in FIG. 1).

Figure 22:
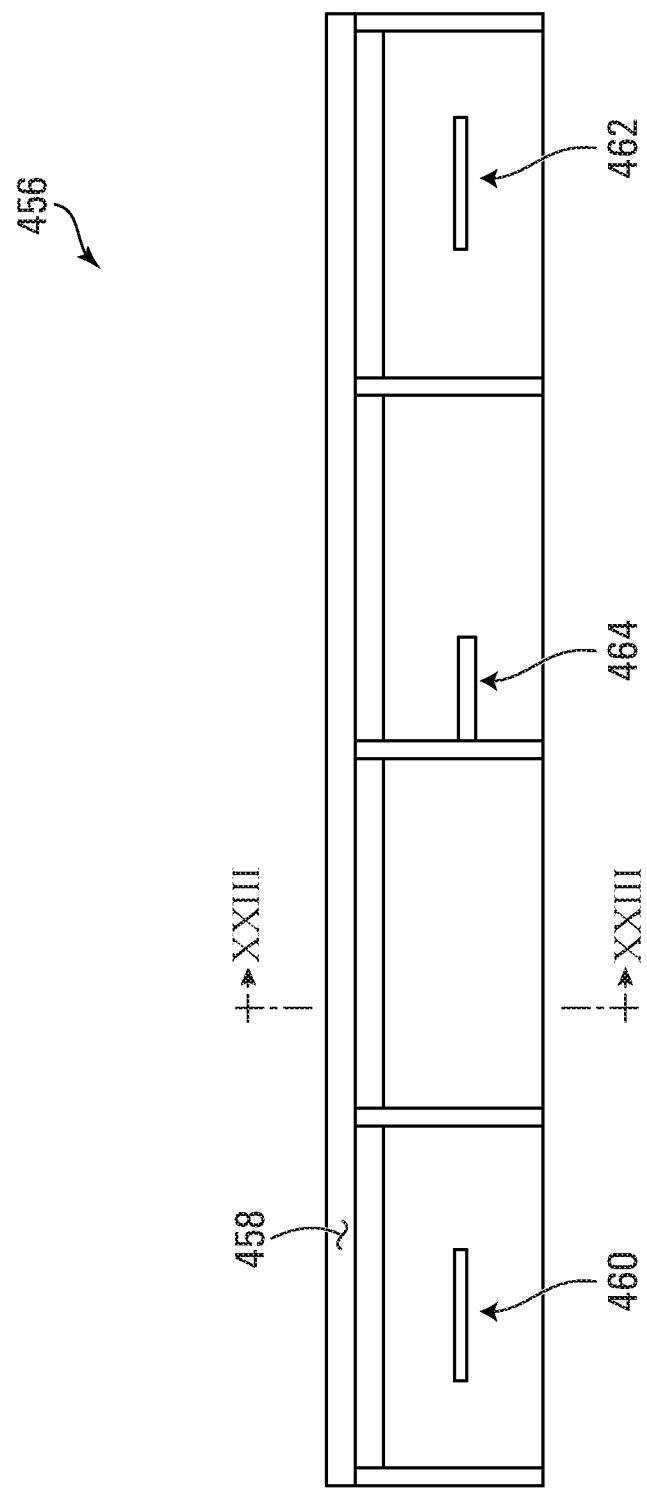
FIG. 22 is a front plan view of an illustrative French cleat.

Referring to FIG. 22, an illustrative French cleat is shown generally at 456 and includes a bevelled edge 458 for contacting one of the bevelled edges 452 and 454 on the body 436 shown in FIG. 21. The bevelled edge 458 of the French cleat 456 thus also functions as a connector. The French cleat 456 also has through-openings shown generally at 460 and 462 for receiving fasteners (not shown) for mounting the French cleat 456 on a wall (such as the wall 88 shown in FIG. 1). The French cleat 456 is thus wall-mountable. The French cleat 456 also includes an inclination measuring device 464, which in the embodiment shown is a bubble level to facilitate mounting the French cleat 456 on a wall (such as the wall 88 shown in FIG. 1) such that the bevelled edge 458 is level.

Figure 23:
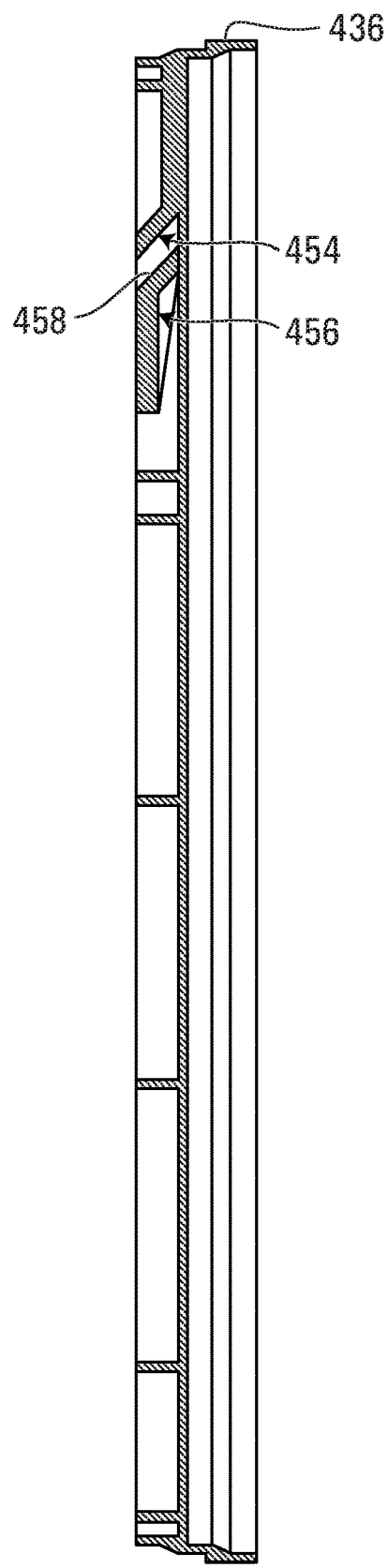
FIG. 23 is a cross-sectional view of an illustrative system including the body of FIG. 21 and the French cleat of FIG. 22 taken along the lines XXIII-XXIII in FIGS. 21 and 22.

Referring to FIG. 23, the body 436 is shown with the bevelled edge 454 of the body 436 nearly in contact with the bevelled edge 458 of the French cleat 456. When the body 436 is lowered relative to the French cleat 456 such that the bevelled edge 454 of the body 436 contacts the bevelled edge 458 of the French cleat 456, the body 436 is supported by the French cleat 456 and thus mounted on the wall. In the embodiment shown, the bevelled edge 454 is longer than the bevelled edge 458, and therefore the body 436 in some embodiments can be moved relative to the French cleat 456 to position the body 436 in a desired position, such as at the head of a bed, for example.

Figure 24:
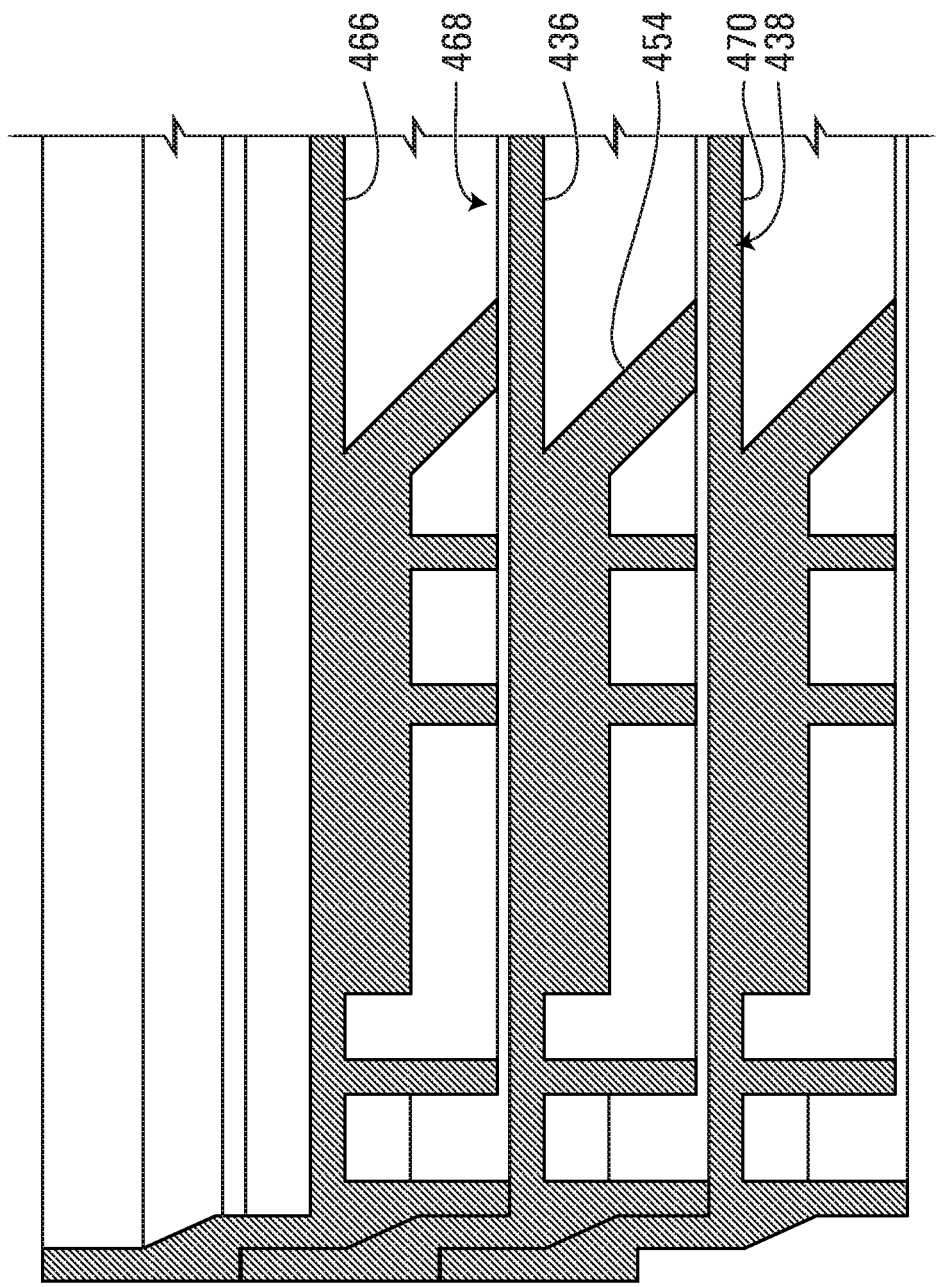
FIG. 24 is a cross-sectional view of an illustrative system including a cross-sectional view of the body of FIG. 21 taken along the line XXIV-XXIV in FIG. 21.

Referring to FIG. 24, an adjacent similar body 466 is stackable against a front side 468 of the body 436, and a similar adjacent body 470 is stackable against the rear side 438 of the body 436.

Figure 26:
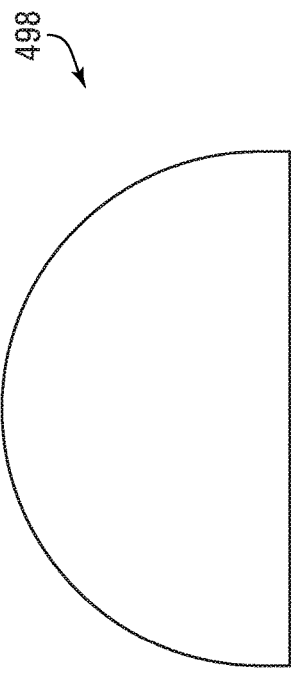
FIG. 26 is a front elevational view of another illustrative body.
Figure 27:
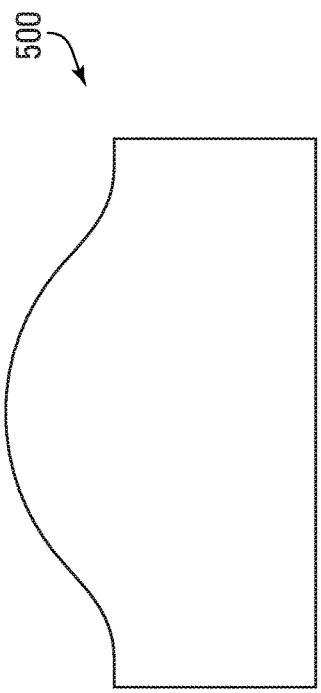
FIG. 27 is a front elevational view of another illustrative body.
Figure 28:
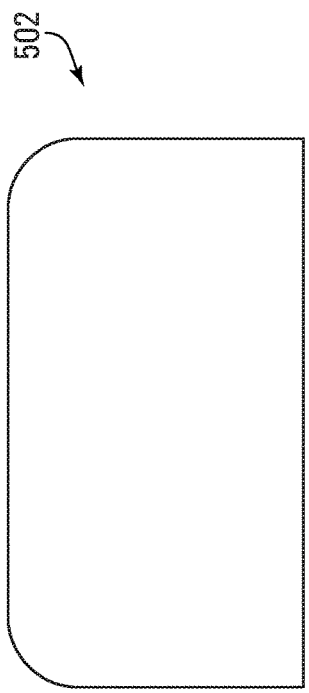
FIG. 28 is a front elevational view of another illustrative body.

The embodiments described above are substantially rectangular, but one skilled in the art will appreciate that other embodiments may have non-rectangular shapes. As illustrative examples, FIG. 26 illustrates a headboard 498 having a shape that may be referred to as an "arched" shape, FIG. 27 illustrates a headboard 500 having a shape that may be referred to as a "camel back" shape, and FIG. 28 illustrates a headboard 502 having a generally rectangular shape with rounded upper corners. It will be appreciated that embodiments such as those illustrated in FIGS. 2 to 25 may alternatively have shapes such as those illustrated in FIGS. 26 to 28, for example.

As indicated above, the bodies disclosed above may form part of headboard systems that hold decorative covers without requiring conventional upholstery techniques and without requiring other more cumbersome alternatives to upholstery. Further, the bodies discussed above may be used to hold decorative covers for applications other than headboards, such as decorating walls more generally, for example. Still further, the bodies discussed above may be stacked as shown in the drawings, for example, and such stacking may permit compact and cost-effective shipping while the contact between adjacent similar bodies stabilizes the bodies during shipping, which may reduce damage during shipping that may be caused from relative movement of adjacent bodies. Further, light sources such as those disclosed above may enhance the visual appearance of walls to which the bodies disclosed above are mounted.

Referring back to FIG. 1, the nightstand 92 includes legs 504, 506, 508, and 510 for contacting the floor 86. The nightstand 92 also includes a generally rectangular frame 512 supported by the legs 504, 506, 508, and 510 over the floor 86, and the nightstand 92 also includes a drawer 514 slidably receivable in the generally rectangular frame 512. In various embodiments, one or more of the legs 504, 506, 508, and 510, the generally rectangular frame 512, and the drawer 514 are substantially thermoplastic bodies of the nightstand, which is a furniture apparatus. One or more of such substantially thermoplastic bodies may be formed in a mold, and in some embodiments, carbon plastic may be desirable because of durability, a polished finish, and various colours that may be available with carbon plastic.

Still further, one or more of such substantially thermoplastic bodies may include incorporated therein one or more of the diatomaceous earth products and legume extracts discussed above. As with the other embodiments discussed, above, such diatomaceous earth, legume extracts, or both may be incorporated into such substantially thermoplastic bodies by adding the diatomaceous earth, the legume extracts, or both to the thermoplastic material when the thermoplastic material is in a liquid phase before the thermoplastic material is injected into a mold. In one embodiment, about 30% by weight of such substantially thermoplastic bodies may be diatomaceous earth or a mixture of diatomaceous earth and one or more legume extracts. Further, additional diatomaceous earth, legume extracts, or both may be adhered to inner surfaces of such substantially thermoplastic bodies, such as inner surfaces of the generally rectangular frame 512 or the drawer 514 for example, for further exposure of the diatomaceous earth to animals such as bedbugs.

In alternative embodiments, the generally rectangular frame 512 and the drawer 514 may be replaced by a table surface platform supported by legs similar to the legs 504, 506, 508, and 510. According to such an embodiment, a furniture apparatus may include a table including substantially thermoplastic bodies and one or both of diatomaceous earth and legume extracts as described above.

Still referring to FIG. 1, the dresser 94 includes a generally rectangular frame 516 and a plurality of drawers, such as the drawers 518 and 520, slidably receivable in the generally rectangular frame 516. The generally rectangular frame 516 and the plurality of drawers slidably receivable therein may be substantially the same as the generally rectangular frame 512 and the drawer 514 described above.

The bed 96 includes a generally rectangular platform 522 for supporting the mattress 98. The bed 96 also includes four substantially thermoplastic bodies at respective corners of the generally rectangular platform 522, and such substantially thermoplastic bodies 524, 526, and 528 are shown in FIG. 1. Such substantially thermoplastic bodies in the embodiment shown are generally cylindrical, and act as supports for contacting the floor 86 and for supporting the generally rectangular platform 522 and thus the mattress 98 above the floor 86. In alternative embodiments, the bed 96 may include more or fewer substantially thermoplastic bodies acting as such supports.

As indicated above, in some embodiments, carbon plastic may be a desirable material for some furniture apparatuses because carbon plastic may be coloured with a desired colour, and externally visible surfaces of the carbon plastic may be polished to reveal the desired colour with a durable and attractive polished finish. Further, in some embodiments, one or more internal surfaces (such as internal surfaces of the generally rectangular frames 512 and 516 shown in FIG. 1, for example, which may be visible when drawers are removed from the generally rectangular frames but otherwise visibly concealed by the drawers) may be darkly coloured, such as coloured black or another dark colour. Thus, when diatomaceous earth, for example, is applied to such internal surfaces, the lighter colour of the diatomaceous earth may make the diatomaceous earth more easily visible on such surfaces, and may facilitate noticing an absence of such products on such surfaces. Therefore, such darkly coloured internal surfaces in some embodiments may assist with visibly determining whether such internal surfaces have been sprayed or otherwise treated with diatomaceous earth or another more lightly coloured product, and such visual determinations may facilitate determining where and when such diatomaceous earth or other products should be applied to ensure a desired amount of such diatomaceous earth or other products on various furniture apparatuses.

Although the nightstand 92, the dresser 94, the bed 96, the mattress 98, and the headboard system 100 are described above, various furniture apparatuses, kits, and systems according to alternative embodiments may include one or more substantially thermoplastic bodies including diatomaceous earth, legume extracts, or both incorporated therein, and such furniture apparatuses according to some embodiments may assist in the control of bedbug and other animal populations. Therefore, commercial use of such apparatuses, kits, and systems may involve distributing, selling, offering for sale, or placing such apparatuses, kits, and systems in bedrooms or hotel rooms in an effort to control populations of animals, such as animals having exoskeletons, arthropods, arachnids, insects, and *Cimex lectularius* for example, in such bedrooms or hotel rooms.

Further, it is believed that bedbugs are often introduced into a bedroom or hotel room from occupants of the bedroom or hotel room, or from the belongings of the occupants of the bedroom or hotel room. It is also believed that such occupants and belongings are likely to be on one or more of a bed, nightstand, and dresser in the bedroom or hotel room, and therefore that bedbugs are likely to be introduced into the bedroom or hotel room in one or more of a bed, nightstand, and dresser in the bedroom or hotel room. It is also believed that bedbugs are likely to dwell in a bed in the bedroom or hotel room. Therefore, in some embodiments, the nightstand 92, the dresser 94, the bed 96, and the headboard system 100 may cooperate with each other and collectively facilitate control of bedbugs by controlling bedbugs in particular locations where bedbugs may be introduced or may likely dwell into the bedroom or hotel room.

Although specific embodiments have been described and illustrated, such embodiments should be considered illustrative of the invention only and not as limiting the invention as construed according to the accompanying claims.

What is claimed is:

1. A headboard apparatus for holding a decorative cover, the apparatus comprising:
    a body having front and rear opposite sides, the front side of the body having a front surface having a perimeter, the rear side of the body having a rear surface, and the body having an outwardly facing lateral surface between the front and rear surfaces; and
    a first connector on the body, the first connector detachably connectable, continuously adjacent at least a portion of the perimeter of the front surface, to a second connector, complementary to the first connector, on the decorative cover;
    wherein the body defines a first projection having the lateral surface and an inward-facing portion of the front surface;
    wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus;
    wherein the body is substantially thermoplastic; and
    wherein the body comprises carbon plastic.

2. The apparatus of claim 1 further comprising a PA1b-related peptide incorporated in the body.

3. A headboard apparatus for holding a decorative cover, the apparatus comprising:
    a body having front and rear opposite sides, the front side of the body having a front surface having a perimeter, the rear side of the body having a rear surface, and the body having an outwardly facing lateral surface between the front and rear surfaces; and
    a first connector on the body, the first connector detachably connectable, continuously adjacent at least a portion of the perimeter of the front surface, to a second connector, complementary to the first connector, on the decorative cover;
    wherein the body defines a first projection having the lateral surface and an inward-facing portion of the front surface;
    wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus;
    wherein the body is substantially thermoplastic; and
    wherein the body comprises diatomaceous earth incorporated in the body.

4. The apparatus of claim 3 wherein the body comprises carbon plastic.

5. The apparatus of claim 3 wherein the diatomaceous earth is about 30% by weight of the body.

6. The apparatus of claim 3 wherein the diatomaceous earth has a median particle diameter of about 15 microns.

7. The apparatus of claim 3 wherein the diatomaceous earth has a median particle diameter of more than about 14 microns.

8. The apparatus of claim 3 further comprising a PA1b-related peptide incorporated in the body.

9. The apparatus of claim 3 wherein the first connector extends adjacent at least a majority of the perimeter of the front surface.

10. The apparatus of claim 3 wherein the first connector extends adjacent substantially the entire perimeter of the front surface.

11. A headboard apparatus of claim 1 for holding a decorative cover, the apparatus comprising:
    a body having front and rear opposite sides, the front side of the body having a front surface having a perimeter, the rear side of the body having a rear surface, and the body having an outwardly facing lateral surface between the front and rear surfaces; and
a first connector on the body, the first connector detachably connectable, continuously adjacent at least a portion of the perimeter of the front surface, to a second connector, complementary to the first connector, on the decorative cover;
wherein the body defines a first projection having the lateral surface and an inward-facing portion of the front surface;
wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus; and
wherein the first connector comprises a hook side or a loop side of a hook-and-loop connector.

12. The apparatus of claim 11 wherein the first connector extends adjacent at least a majority of the perimeter of the front surface.

13. The apparatus of claim 11 wherein the first connector extends adjacent substantially the entire perimeter of the front surface.

14. The apparatus of claim 11 wherein the first connector is on the lateral surface.

15. A headboard apparatus further for holding a decorative cover, the apparatus comprising:
a body having front and rear opposite sides, the front side of the body having a front surface having a perimeter, the rear side of the body having a rear surface, and the body having an outwardly facing lateral surface between the front and rear surfaces;
a first connector on the body, the first connector detachably connectable, continuously adjacent at least a portion of the perimeter of the front surface, to a second connector, complementary to the first connector, on the decorative cover; and
a third connector on the rear side of the apparatus for mounting the rear side of the apparatus on a wall separate from the apparatus and separate from the decorative cover;
wherein the body defines a first projection having the lateral surface and an inward-facing portion of the front surface; and
wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus.

16. The apparatus of claim 15 wherein the first connector is on the lateral surface.

17. A headboard apparatus for holding a decorative cover, the apparatus comprising:
a body having front and rear opposite sides, the front side of the body having a front surface having a perimeter, the rear side of the body having a rear surface, and the body having an outwardly facing lateral surface between the front and rear surfaces; and
a first connector on the body, the first connector detachably connectable, continuously adjacent at least a portion of the perimeter of the front surface, to a second connector, complementary to the first connector, on the decorative cover;
wherein:
the body defines a first projection having the lateral surface and an inward-facing portion of the front surface;
at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus;
the front surface defines a recess for receiving padding between the body and the decorative cover;
the front surface comprises a generally flat planar portion and the inward-facing portion between the generally flat planar portion and the lateral surface of the body; and
the generally flat planar portion of the front surface and the inward-facing portion of the front surface define the recess.

18. A headboard apparatus for holding a decorative cover, the apparatus comprising:
a body having front and rear opposite sides, the front side of the body having a front surface having a perimeter, the rear side of the body having a rear surface, and the body having an outwardly facing lateral surface between the front and rear surfaces;
a first connector on the body, the first connector detachably connectable, continuously adjacent at least a portion of the perimeter of the front surface, to a second connector, complementary to the first connector, on the decorative cover;
a bed frame connector for connecting the body to a bed frame, wherein the bed frame connector comprises at least one receptacle defined by the body for receiving at least one respective support attachable to the bed frame; and
the at least one support receivable in the respective at least one receptacle and attachable to the bed frame;
wherein the body defines a first projection having the lateral surface and an inward-facing portion of the front surface; and
wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus.

19. The apparatus of claim 18 wherein the first connector is on the lateral surface.

20. A kit comprising:
a headboard apparatus for holding a decorative cover, the apparatus comprising:
a body having front and rear opposite sides, the front side of the body having a front surface having a perimeter, the rear side of the body having a rear surface, and the body having an outwardly facing lateral surface between the front and rear surfaces; and
a first connector on the body, the first connector detachably connectable, continuously adjacent at least a portion of the perimeter of the front surface, to a second connector, complementary to the first connector, on the decorative cover;

wherein the body defines a first projection having the lateral surface and an inward-facing portion of the front surface; and wherein at least a portion of the lateral surface is positioned to contact at least a portion of the inward-facing portion of the front surface of an adjacent similar apparatus such that the adjacent similar apparatus is stackable against the rear side of the body when the at least the portion of the lateral surface contacts the at least the portion of the inward-facing portion of the front surface of the adjacent similar apparatus; and the decorative cover, wherein when the first connector is connected to the second connector, the decorative cover covers at least a portion of the front surface of the body surrounded by the perimeter of the front surface of the body.

21. The kit of claim 20 further comprising padding, wherein the front surface defines a recess for receiving the padding between the body and the decorative cover.

\* \* \* \* \*